US010126438B2

(12) United States Patent
Cates, Jr. et al.

(10) Patent No.: US 10,126,438 B2
(45) Date of Patent: Nov. 13, 2018

(54) SYSTEMS AND METHODS FOR POLARIZED NUCLEAR IMAGING AND SPECTROSCOPY

(71) Applicant: UNIVERSITY OF VIRGINIA PATENT FOUNDATION, Charlottesville, VA (US)

(72) Inventors: Gordon D. Cates, Jr., Gordonsville, VA (US); G. Wilson Miller, Charlottesville, VA (US); Yuan Zheng, Fremont, CA (US); William A. Tobias, Charlottesville, VA (US)

(73) Assignee: UNIVERSITY OF VIRGINIA PATENT FOUNDATION, Charlottesville, VA (US)

( * ) Notice: Subject to any disclaimer, the term of this patent is extended or adjusted under 35 U.S.C. 154(b) by 645 days.

(21) Appl. No.: 14/859,271

(22) Filed: Sep. 19, 2015

(65) Prior Publication Data
US 2016/0084971 A1 Mar. 24, 2016

Related U.S. Application Data

(60) Provisional application No. 62/052,797, filed on Sep. 19, 2014.

(51) Int. Cl.
*G01T 1/29* (2006.01)
*G01R 33/26* (2006.01)
(Continued)

(52) U.S. Cl.
CPC ............ *G01T 1/2985* (2013.01); *G01R 33/46* (2013.01); *G01R 33/481* (2013.01);
(Continued)

(58) Field of Classification Search
CPC ...... G01R 33/46; G01R 33/481; G01R 33/50; G01R 33/5601; G01T 1/1603; G01T 1/2985
See application file for complete search history.

(56) References Cited

U.S. PATENT DOCUMENTS

| 4,047,037 A | 9/1977 | Schlosser et al. |
| H000012 H | 1/1986 | Bennett et al. |

(Continued)

FOREIGN PATENT DOCUMENTS

| EP | 1132756 A2 | 9/2001 |
| EP | 1132757 A2 | 9/2001 |

OTHER PUBLICATIONS

Albert, M.S. et al., "Biological magnetic resonance imaging using laser-polarized 129Xe," Nature, 1994, pp. 199-201, 370(6486).
(Continued)

*Primary Examiner* — Michael Rozanski
(74) *Attorney, Agent, or Firm* — Meunier Carlin & Curfman LLC

(57) ABSTRACT

Some aspects of the present disclosure relate to systems and methods for examining a subject. In one embodiment, a method includes polarizing nuclei of a radioactive substance such that the spins of the nuclei are oriented in a specific direction, to generate a polarized radioactive tracer with anisotropic gamma ray emission probability. The method also includes introducing the tracer into a subject. The method further includes applying radio frequency oscillating (RF) magnetic fields and/or spatially varying magnetic fields to the tracer that are configured to manipulate the orientation of the spins such as to manipulate the directional dependence of gamma ray emission from the tracer. The method further includes detecting gamma rays from the gamma ray emission, and obtaining, based on the detected gamma rays and properties associated with the anisotropic gamma ray emission, imaging data and/or spectroscopic data associated with the tracer in the subject.

39 Claims, 16 Drawing Sheets

(51) Int. Cl.
G01R 33/38 (2006.01)
G01R 33/46 (2006.01)
G01R 33/48 (2006.01)
G01R 33/56 (2006.01)
G01T 1/16 (2006.01)
G01R 33/50 (2006.01)

(52) U.S. Cl.
CPC ........ G01R 33/5601 (2013.01); G01T 1/1603 (2013.01); *G01R 33/50* (2013.01)

(56) References Cited

U.S. PATENT DOCUMENTS

| | | | |
|---|---|---|---|
| 5,276,615 | A | 1/1994 | Edmond et al. |
| 5,545,396 | A | 8/1996 | Albert et al. |
| 5,608,221 | A | 3/1997 | Bertelsen et al. |
| 5,642,625 | A | 7/1997 | Cates, Jr. et al. |
| 5,779,637 | A | 7/1998 | Palkovich et al. |
| 5,785,953 | A | 7/1998 | Albert et al. |
| 5,789,921 | A | 8/1998 | Albert et al. |
| 5,809,801 | A | 9/1998 | Cates, Jr. et al. |
| 5,860,295 | A | 1/1999 | Cates, Jr. et al. |
| 5,929,446 | A | 7/1999 | Plummer et al. |
| 5,936,404 | A | 8/1999 | Ladebeck et al. |
| 6,008,644 | A | 12/1999 | Leunbach et al. |
| 6,031,373 | A | 2/2000 | Szeles et al. |
| 6,051,208 | A | 4/2000 | Johnson et al. |
| 6,123,919 | A | 9/2000 | Albert et al. |
| 6,241,966 | B1 | 6/2001 | Albert et al. |
| 6,346,229 | B1 | 2/2002 | Driehuys et al. |
| 6,358,194 | B1 | 3/2002 | Van Deripe |
| 6,818,202 | B2 | 11/2004 | Pines et al. |
| 6,942,467 | B2 | 9/2005 | Deninger et al. |
| 7,174,200 | B2 | 2/2007 | Salerno et al. |
| 7,402,813 | B2 | 7/2008 | Ben-Haim et al. |
| 7,718,971 | B2 | 5/2010 | Tanaka |
| 8,242,453 | B2 | 8/2012 | Wieczorek |
| 8,723,128 | B2 | 5/2014 | Takayama |
| 2003/0036700 | A1* | 2/2003 | Weinberg ............... A61B 6/425 600/436 |
| 2005/0161606 | A1 | 7/2005 | Balan et al. |
| 2012/0232381 | A1 | 9/2012 | Gilhuijs et al. |
| 2013/0259805 | A1 | 10/2013 | Bacskai |
| 2013/0338490 | A1 | 12/2013 | Wendler |

OTHER PUBLICATIONS

Calaprice, F. et al., "Nuclear Alignment and Magnetic Moments of 133Xe, 133Xem, and 131Xem by Spin Exchange with Optically Pumped 87Rb," Phys. Rev. Lett., 1985, pp. 174-177, 54(3).

Driehuys, B. et al., "High-volume production of laser-polarized 129Xe," Appl. Phys. Lett., 1996, p. 1668, 69(12).

Kauczor, H. et al., "MRI using hyperpolarized noble gasses," Eur. Radiol. 1998, pp. 820-827, 8(5).

Myers, W.G. et al., "Krypton-79m: a new radionuclide for applications in nuclear medicine," J. Nucl. Med., 1986, pp. 1436-1441, 27(9).

Rabi, I.I., "Space Quantization in a Gyrating Magnetic Field," Phys. Rev., 1937, pp. 652-654, 51(8).

Walker, T.G. et al., "Spin-exchange optical pumping of noble-gas nuclei," Reviews of Modem Physics, 1997, pp. 529-642, 69(2).

Wu, Z. et al., "Coherent Nuclear-Spin Interactions of Adsorbed 131Xe Gas with Surfaces," Phys. Rev. Lett., 1987, pp. 1480-1483, 59(13).

Yamazaki, T., "Tables of coefficients for angular distribution of gamma rays from aligned nuclei," Nuclear Data Sheets, Section A, 1967, pp. 1-23, 3(1).

Zheng, Y. et al., "Very-low-field MRI of laser polarized xenon-129," J. Magn. Reson., 2014, pp. 108-117, vol. 249, Elsevier, Inc.

Berthault, P. et al., "Biosensing using laser-polarized xenon NMR/MRI," Prog. Nucl. Magn. Reson. Spectrosc., 2009, pp. 35-60, 55(1), Elesevier B.V.

Bonn, J. et al., "Orientation of 199mHg by Optical Pumping Detected by γ-Radiation Anisotropy," Z. Physik A, 1975, pp. 375-380, 272(4), Springer-Verlag.

3APPELLER, U. et al., "Anisotropy and time modulation of γ-radiation emitted by optically aligned 203Hg nuclei," J. Magn. Reson., 1969, pp. 15-21, 10(1), Elsevier Science B.V.

Ernst, R.R., "Nuclear Magnetic Resonance Fourier Transform Spectroscopy (Noble Lecture)," Angew. Chem. Int. Ed., 1992, pp. 805-823, 31(7), Nobel Foundation.

Jastram, P.S. et al., "Angular Correlation of Gamma Radiations from Oriented Nuclei," Phys. Rev., 1956, pp. 1381-1388, 101(4).

Lauterbur, P.C., "Image Formation by Induced Local Interactions: Examples Employing Nuclear Magnetic Resonance," Nature, 1973, pp. 190-191, vol. 242, Nature Publishing Group.

Myers, W.G. et al., "Xenon-127m: A New Radionuclide for Applications in Nuclear Medicine," J. Nucl. Med., 1990, pp. 489-492, 31(4).

Mugler III, J.P. et al., "Simultaneous magnetic resonance imaging of ventilation distribution and gas uptake in the human lung using hyperpolarized xenon-129," Proceedings of the National Academy of Sciences, 2010, pp. 21707-21712, 107(50), National Academy of Sciences.

Mugler III, J.P. et al., "Hyperpolarized 129Xe MRI of the human lung," J. Magn. Reson. Imaging, 2013, pp. 313-331, 37(2), Wiley Periodicals, Inc.

Rabi, I.I. et al., "A New Method of Measuring Nuclear Magnetic Moment," Phys. Rev., 1938, p. 318, 53(4).

Rodriguez, J. et al., "Determination of spin, magnetic moment and isotopic shift of neutron rich205Hg by optical pumping," Z. Physik A., 1975, pp. 369-374, 272(4), Springer-Verlag.

Spence, M.M. et al., "Functionalized xenon as a biosensor," Proceedings of the National Academy of Sciences, 2001, pp. 10654-10657, 98(19), National Academy of Sciences.

Spiers, J.A., "Angular Distribution of Radioactive Disintegration Products," Nature, 1948, pp. 807-809, vol. 161, Nature Publishing Group.

Tolhoek, H.A. et al., "Angular distribution and polarization of gamma radiation emitted by aligned radioactive nuclei," Physica XVIII, Letter to the Editor, 1952, pp. 357-358, No. 5.

Tolhoek, H.A. et al., "Angular Distribution and Polarization of Gamma Radiation Emitted by Oriented Nuclei," Physica XIX, 1953, pp. 101-119.

International Search Report and Written Opinion for related International Application No. PCT/US15/53403 dated Dec. 29, 2015.

* cited by examiner

SYSTEMS AND METHODS FOR POLARIZED NUCLEAR IMAGING AND SPECTROSCOPY

CROSS-REFERENCE TO RELATED APPLICATION

This Application claims priority to and benefit under 35 U.S.C § 119(e) of U.S. Provisional Patent Application Ser. No. 62/052,797 filed Sep. 19, 2014, which is hereby incorporated by reference herein in its entirety as if fully set forth below.

Some references, which may include patents, patent applications, and various publications, are cited in a reference list and discussed in the disclosure provided herein. The citation and/or discussion of such references is provided merely to clarify the description of the present disclosure and is not an admission that any such reference is "prior art" to any aspects of the present disclosure described herein. All references cited and discussed in this specification are incorporated herein by reference in their entireties and to the same extent as if each reference was individually incorporated by reference. In terms of notation, hereinafter, "[n]" represents the $n^{th}$ reference cited in the reference list. For example, [4] represents the 4th reference cited in the reference list, namely B. Driehuys et al., *High-Volume Production of Laser-Polarized $^{129}Xe$*, Appl. Phys. Lett. 69, 1668 (1996).

BACKGROUND

A wide variety of diagnostic techniques exist in the practice of medicine, including imaging modalities such as X-ray tomography, magnetic resonance imaging (MRI), and various nuclear-medicine imaging techniques. Molecular imaging techniques can use a tracer that is introduced to the body of a subject and selectively absorbed by parts of the body in which specific physiological processes are occurring, for example malignant tumor growth. An image of the body in such situations can selectively highlight both primary and secondary tumors, which can be extremely important in evaluating the progression of cancer.

In addition to imaging techniques, non-imaging diagnostic procedures also play an important role in medicine. Beyond the wide variety of blood tests that are available, for instance, other techniques may directly measure glomerular filtration rate (GFR), which can be a good measure of kidney function, where the standard are measurements of inulin clearance rate, a procedure that involves the infusion of inulin, and ongoing sampling of blood and urine to track the rate at which inulin is cleared from the blood. This test takes a considerable length of time to perform. For this reason, physicians may rely instead on indirect measurements of GFR based on serum creatinine levels coupled with data on body type. Among other possible needs, the inventors of the present disclosure have recognized that a GFR test that could be performed in real time could be of considerable value in identifying and managing acute kidney injury, or even the existence of chronic kidney problems that might contraindicate the use of contrast agents such as iodine.

With respect to existing imaging modalities, MRI can provide high detail, particularly of soft tissue. This technique may also be tailored so that contrast reflects morphology and also function and physiological processes. It has been recognized that longitudinal and transverse spin relaxation rates, $1/T_1$ and $1/T_2$, are different in tumor and healthy tissues. Differences in blood flow can also be translated into MRI contrast, a technique that has been central to functional MRI (fMRI) studies of the brain. MRI can have the drawback, however, that a relatively large number of nuclear spins is needed to get reasonable signal-to-noise (SNR).

In contrast to MRI, nuclear-medicine studies may utilize a variety of radioactive tracers that are explicitly introduced into the subject. These tracers can be chemically attached to various molecules that are selectively absorbed by the body, making it possible to probe specific processes or potential pathologies within the body. Detection can be accomplished through gamma-ray detection, and with the exception of positron emission tomography (PET) studies, imaging may rely on the use of gamma-ray cameras, which may be composed of an array of gamma detectors.

Because gamma-ray cameras use collimators, however, they may detect only a small number of the gamma rays incident upon them. Resolution is generally quite limited as a result.

In the mid 1990's, it was shown that certain noble gases, such as $^{129}Xe$ and $^{3}He$, laser-polarized using the technique of spin-exchange optical pumping ([1]) could be used to image the gas space of lungs with unprecedented resolution ([2]). Xenon is lipophilic, and is known to dissolve into the blood stream; it is used both as anesthetic and as a contrast agent for CT of the brain. There has thus been interest in using laser-polarized $^{129}Xe$ to probe parts of the body other than the lungs, but due to the limited amount of $^{129}Xe$ that is delivered to distill parts of the body, and the small resulting signals, there has been only limited research in this area.

Despite the early work described in reference [3], the techniques of pulse NMR have not been employed while monitoring the nuclei using gamma detection. Furthermore, the question of whether pulse NMR techniques can be used to image radioactive isotopes while using spatial anisotropies in the emission of gamma rays as a means of detection has not been explored. This may be due to the fact that there are several important differences between detecting spatial anisotropies in gamma emission and the types of RF electromagnetic signals that are detected in magnetic resonance (MR) studies.

It is with respect to these and other considerations that the various embodiments described below are presented.

SUMMARY

Some aspects of the present disclosure relate to systems and methods for examining a subject. Among other benefits and advantages of practicing aspects of the present disclosure, data from gamma detection can be used to reconstruct both images and non-imaging diagnostic information.

In one aspect, the present disclosure relates to a method for examining a subject, which in one embodiment includes polarizing nuclei of a radioactive substance such that the spins of the nuclei are oriented in a specific direction, to generate a polarized radioactive tracer with anisotropic gamma ray emission probability. The method also includes introducing the tracer into a subject. The method further includes applying radio frequency oscillating (RF) magnetic fields and/or spatially varying magnetic fields to the tracer that are configured to manipulate the orientation of the spins such as to manipulate the directional dependence of gamma ray emission from the tracer. The method further includes detecting gamma rays from the gamma ray emission, and obtaining, based on the detected gamma rays and properties associated with the anisotropic gamma ray emission, imaging data and/or spectroscopic data associated with the tracer in the subject.

In another aspect, the present disclosure relates to a system for examining a subject, which in one embodiment includes a polarizing system configured to polarize nuclei of a radioactive substance such that the spins of the nuclei are oriented in a specific direction, to generate a polarized radioactive tracer with anisotropic gamma ray emission probability. The polarized radioactive tracer is introduced into a subject to be examined. The system also includes a first magnetic field source configured to apply radio frequency oscillating (RF) magnetic fields to manipulate the orientation of the spins and/or a second magnetic field source configured to apply spatially varying magnetic fields to manipulate the orientation of the spins. Each of the first magnetic field source and second magnetic field source is configured to manipulate the orientation of the spins such as to manipulate the directional dependence of gamma ray emission from the tracer. The system further includes one or more gamma detectors configured to detect gamma rays from the gamma ray emission, and also includes an imaging system and/or spectroscopy system configured to obtain, based on the detected gamma rays and properties associated with the anisotropic gamma ray emission, imaging data and/or spectroscopic data, respectively, that is associated with the tracer in the subject.

Other aspects and features according to the present disclosure will become apparent to those of ordinary skill in the art, upon reviewing the following detailed description in conjunction with the accompanying figures.

BRIEF DESCRIPTION OF THE DRAWINGS

Reference will now be made to the accompanying drawings, which are not necessarily drawn to scale.

FIG. 3A shows Helmholtz coils that can provide the holding field (with their symmetry axis along the z-axis), the RF coils, with their symmetry axis along the y-axis, and the transverse and longitudinal detectors, aligned with the x- and z-axes respectively. FIG. 3B shows gradient coils separately for clarity.

pulse, gradient pulses are applied, and then a second $$\frac{\pi}{2}$$

pulse is appnea, flipping a sunset of the spin back into the longitudinal direction. The ADC is then opened, where the primary signal comes from the two longitudinal detectors.

Figure 5:
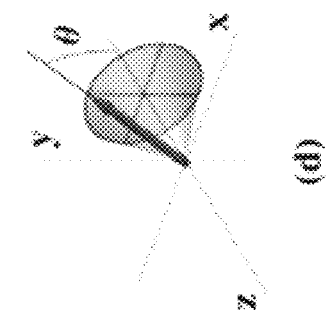
Figure 5:
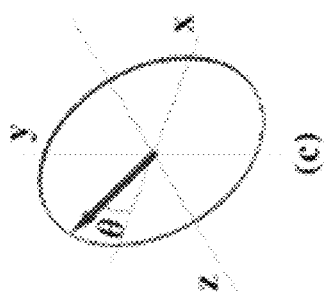
Figure 5:
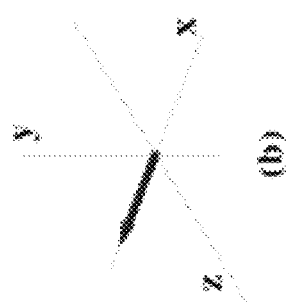
Figure 5:
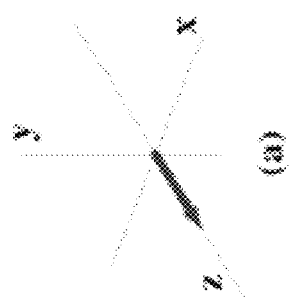

FIG. 5 illustrates a CMZ pulse sequence in accordance with an embodiment of the present disclosure, with static longitudinal readout. In a), the spins are initially aligned parallel to the magnetic field in the z direction. In b), the spins have been tipped by $$\frac{\pi}{2}$$

such that that they are parallel to the x axis through the application of an oscillating field in the y direction. In c), the spins are shown making an angle θ with respect to the x axis due to precessing around the z axis. The precession is due both to the static holding field as well as magnetic-field gradients. In d), the spins have been subjected to a second $$\frac{\pi}{2}$$

pulse, causing the spins to ne rotated into the y-z plane, where they will proceed to precess about the z axis.

Figure 6:
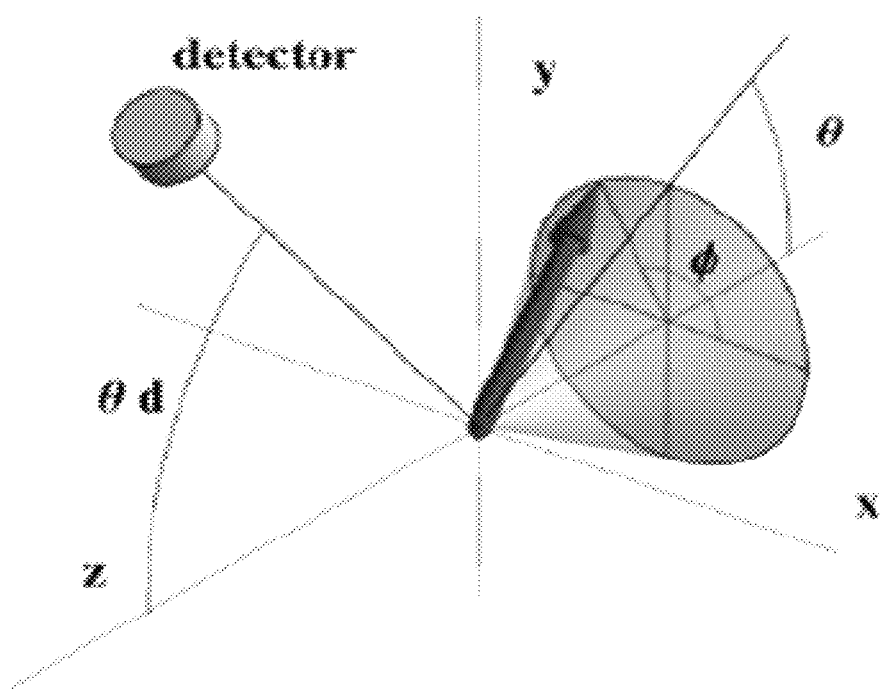

FIG. 6 demonstrates a geometry, in accordance with an embodiment of the present disclosure, that can be used to consider the count rate in an off-axis detector in the y-z plane that makes an angle $\theta_d$ with respect to the z-axis. The gammas being detected are due to an ensemble of precessing spins at the origin whose polarization is at an angle θ with respect to the z-axis.

Figure 7:
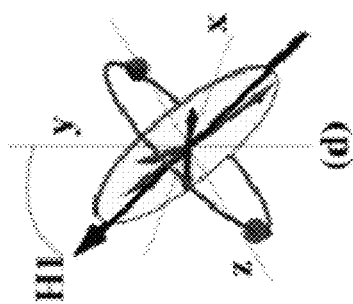
Figure 7:
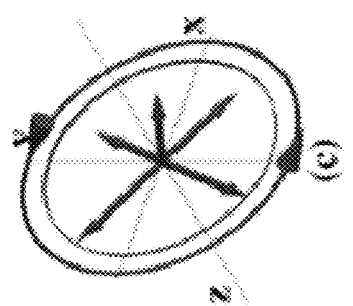
Figure 7:
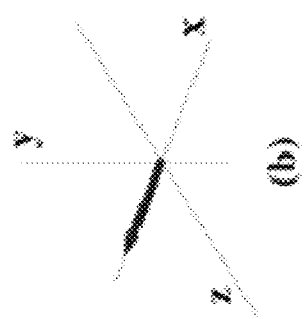
Figure 7:
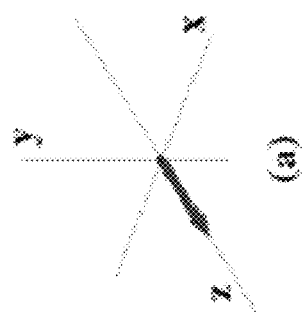

FIG. 7 illustrates a process for generating CMZ pulse sequence with spin locking, in accordance with an embodiment of the present disclosure. Shown in a), the spins are polarized longitudinally along the z-axis. In b), through the application of an RF field along the y-axis, the spins are rotated by $$\frac{\pi}{2}$$

so that they lie parallel to the x-axis. In c), through the application of magnetic-field gradients, the spins fan out in the x-y plane. In d), an RF field is again applied, causing the projection of spin along $H_1$ to be maintained and to rotate in the x-y planes.

Figure 8:
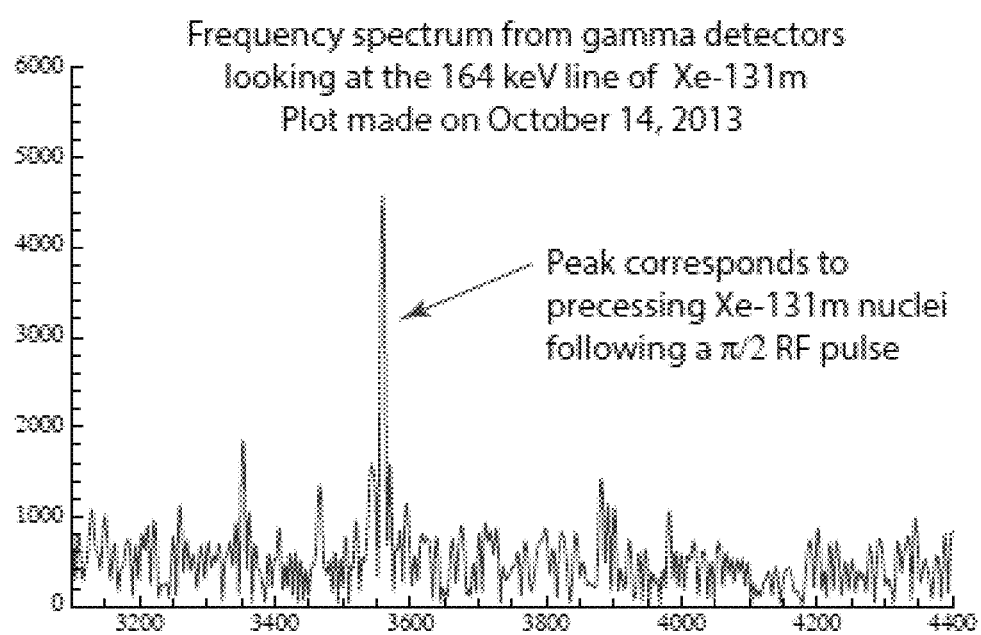

FIG. 8 illustrates, with respect to EXAMPLE 1, polarized nuclear spectroscopy (PNS) according to an embodiment of the present disclosure, with pulse NMR using only gamma detection. The Fourier transform of the signals from two gamma detectors in the transverse plane (see system shown in FIG. 2) is following a $$\frac{\pi}{2}$$

pulse. t peak corresponuing to twice the Larmor frequency of $^{131m}$Xe is seen at the expected frequency.

Figure 9:
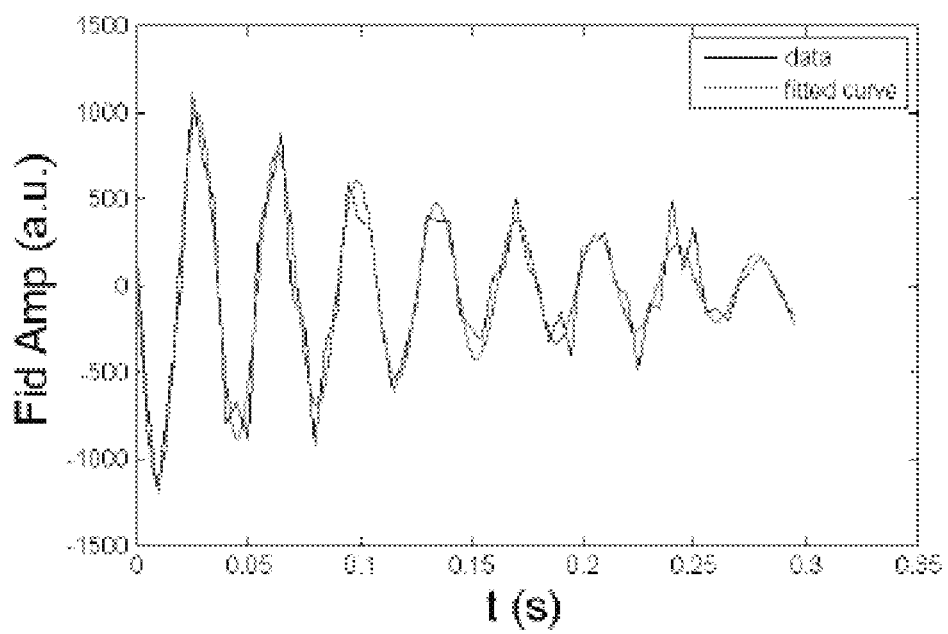

FIG. 9 illustrates, with respect to EXAMPLE 1, a free induction decay obtained by PNS of $^{131m}$Xe, made by mixing down to a lower frequency, according to an embodiment of the present disclosure. The effective T2 may be limited by quadropole interactions.

Figure 10:
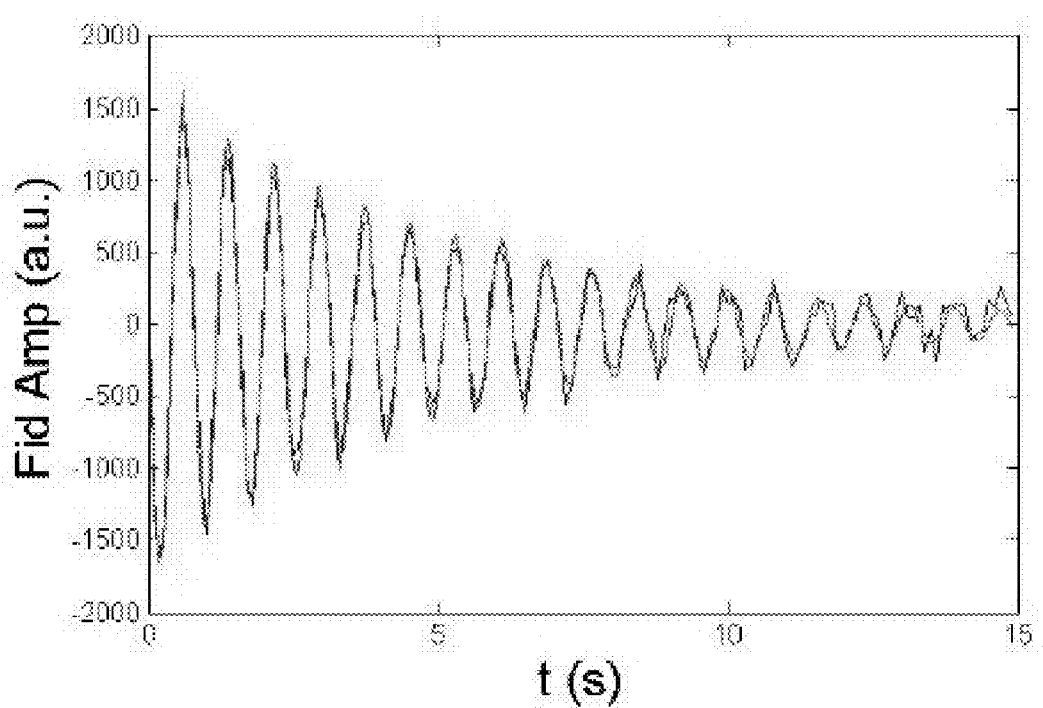

FIG. 10 illustrates, with respect to EXAMPLE 2, a precession signal from $^{131m}$Xe precessing under spin-locked conditions. A fit with an exponentially damped sinusoid yields 5.2 seconds.

Figure 11:
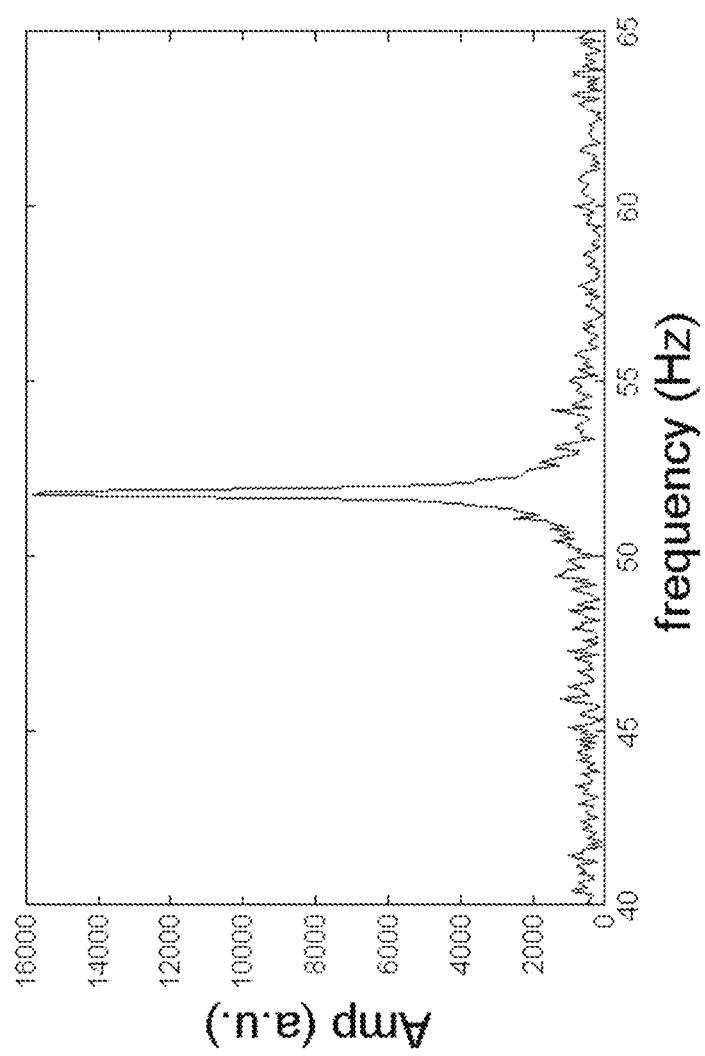

FIG. 11 illustrates, with respect to EXAMPLE 3, a frequency spectrum obtained from a sample of $^{131m}$Xe using Rabi Precession Spectroscopy with gamma detection, in accordance with an embodiment of the present disclosure.

Figure 12:
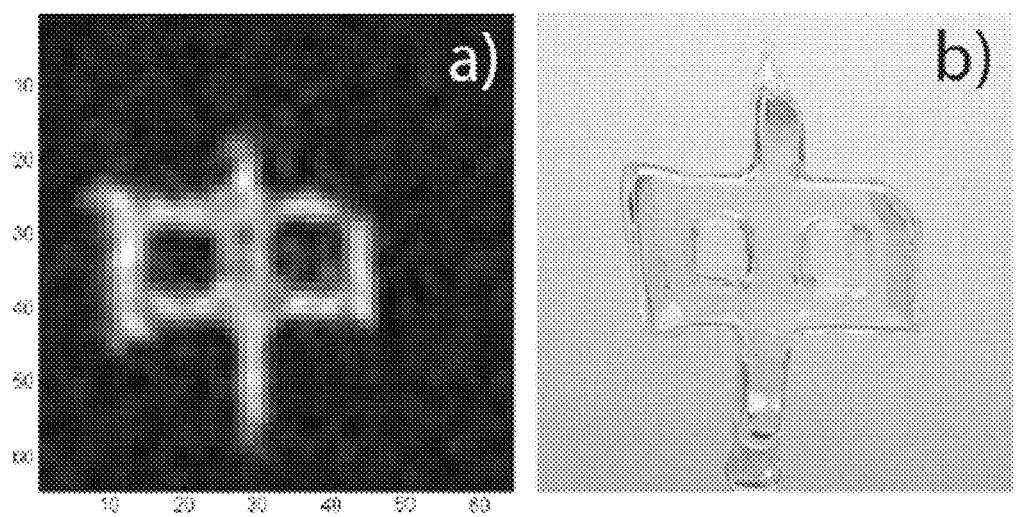

FIG. 12 illustrates, with respect to EXAMPLE 4, an image (13a) demonstrating the viability of polarized nuclear imaging (PNI) in accordance with various embodiments of the present disclosure. The image 13a corresponds to the glass phantom that is shown in b), which resembles the Chinese character for "middle", obtained by PNI. A CMZ pulse sequence in accordance with an embodiment of the present disclosure was used to acquire an image and take advantage of the very small quantity of $^{131m}$Xe available. The pixel size is 3 mm by 3 mm, and there is no slice selection. The image in a) was obtained with between 1 and 2 milli-Curies of $^{131}$Xe.

Figure 13:
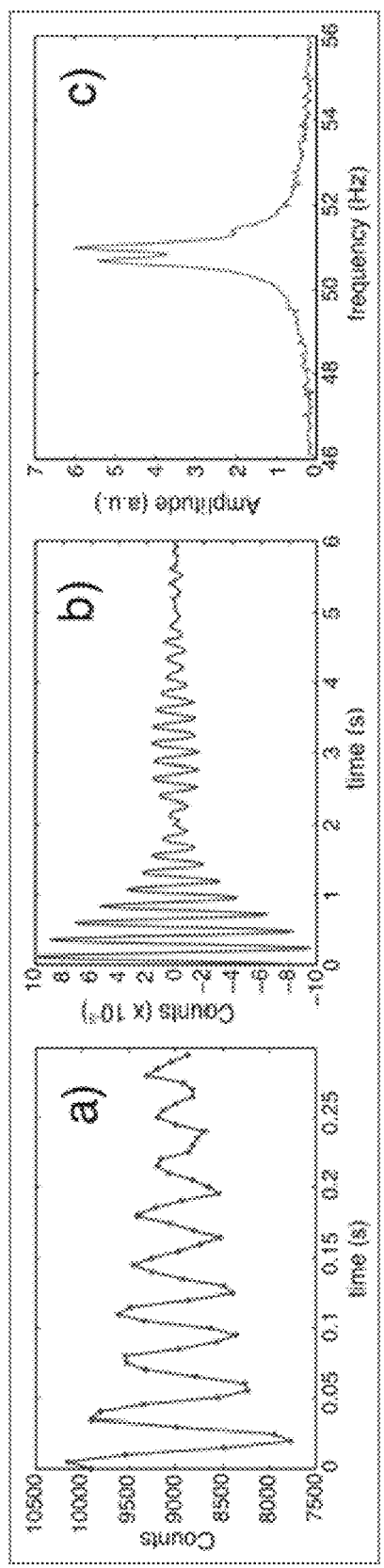

FIG. 13 illustrates, with respect to EXAMPLE 4, graphical representations of several sets of measurements using transverse detectors to monitor the precession of polarized $^{131m}$Xe in accordance with an embodiment of the present disclosure. In a), a free-induction decay of $^{131m}$Xe using only gamma-ray detection is shown. In b), counts versus time in the transverse detectors during Rabi oscillations are shown, where data was processed and mixed to a lower frequency to emphasize the oscillations, according to an embodiment of the present disclosure. In c), the Fourier transform of counts versus time in the longitudinal detector is shown before modulation.

Figure 14:
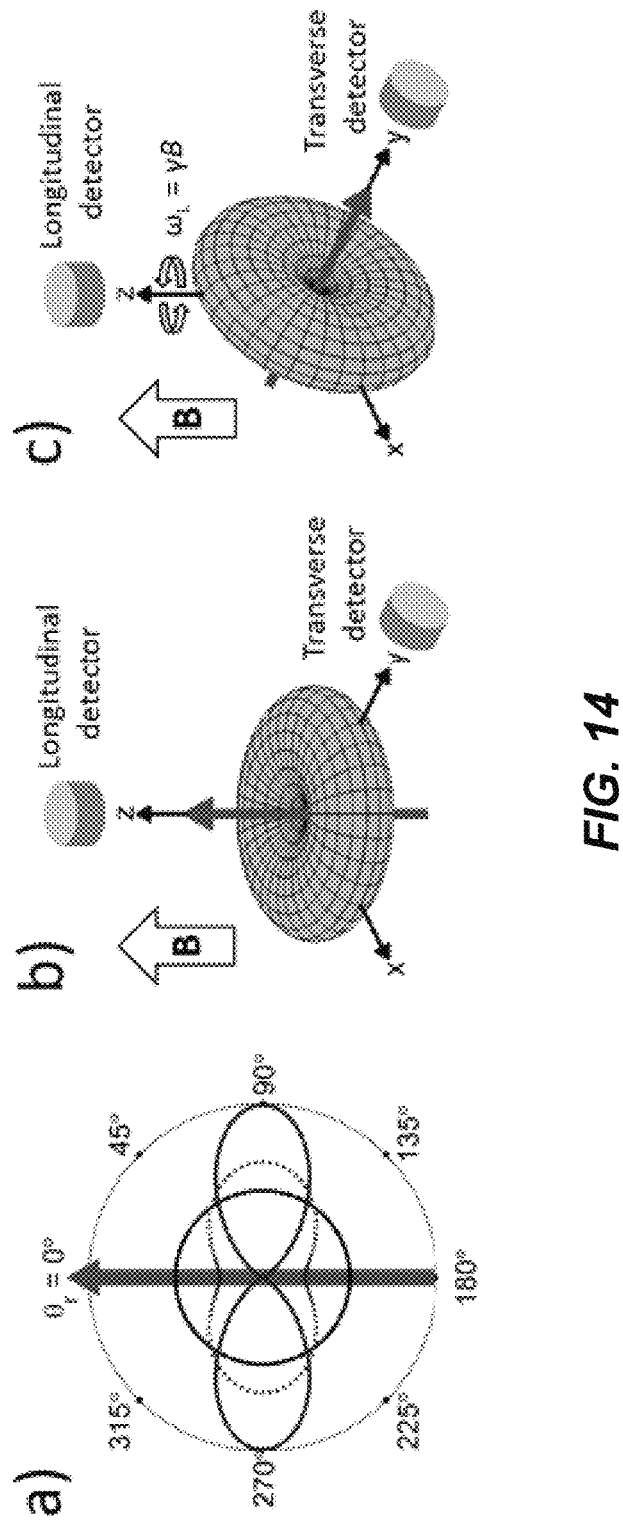

FIG. 14 illustrates, with respect to EXAMPLE 4, directional-emission-probability distributions of 164 keV gamma rays from $^{131m}$Xe nuclei, according to an embodiment of the present disclosure. In a), a polar plot of Eq. 1 (below) as a function of the angle $\theta_r$ with respect to the direction of orientation (red arrow) is shown for an ensemble of nuclei with polarization of 0%, 70%, and 100% respectively. In b) a 3D representation of Eq. 1 for 100% polarized $^{131m}$Xe nuclei oriented along an applied magnetic field B is shown. In c), the directional emission probability of 100% polarized $^{131m}$Xe nucleus oriented in the transverse (x-y) plane is shown.

Figure 15:
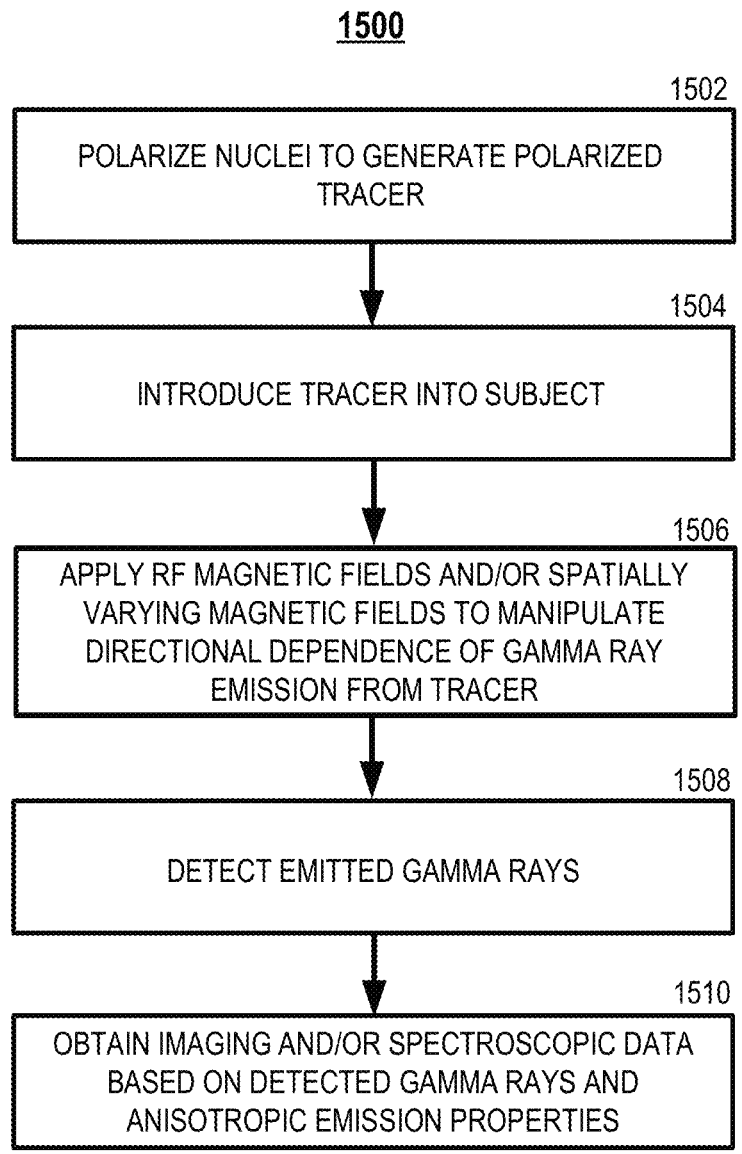

FIG. 15 is a flowchart representation of a method for examining a subject, in accordance with an embodiment of the present disclosure.

Figure 16:
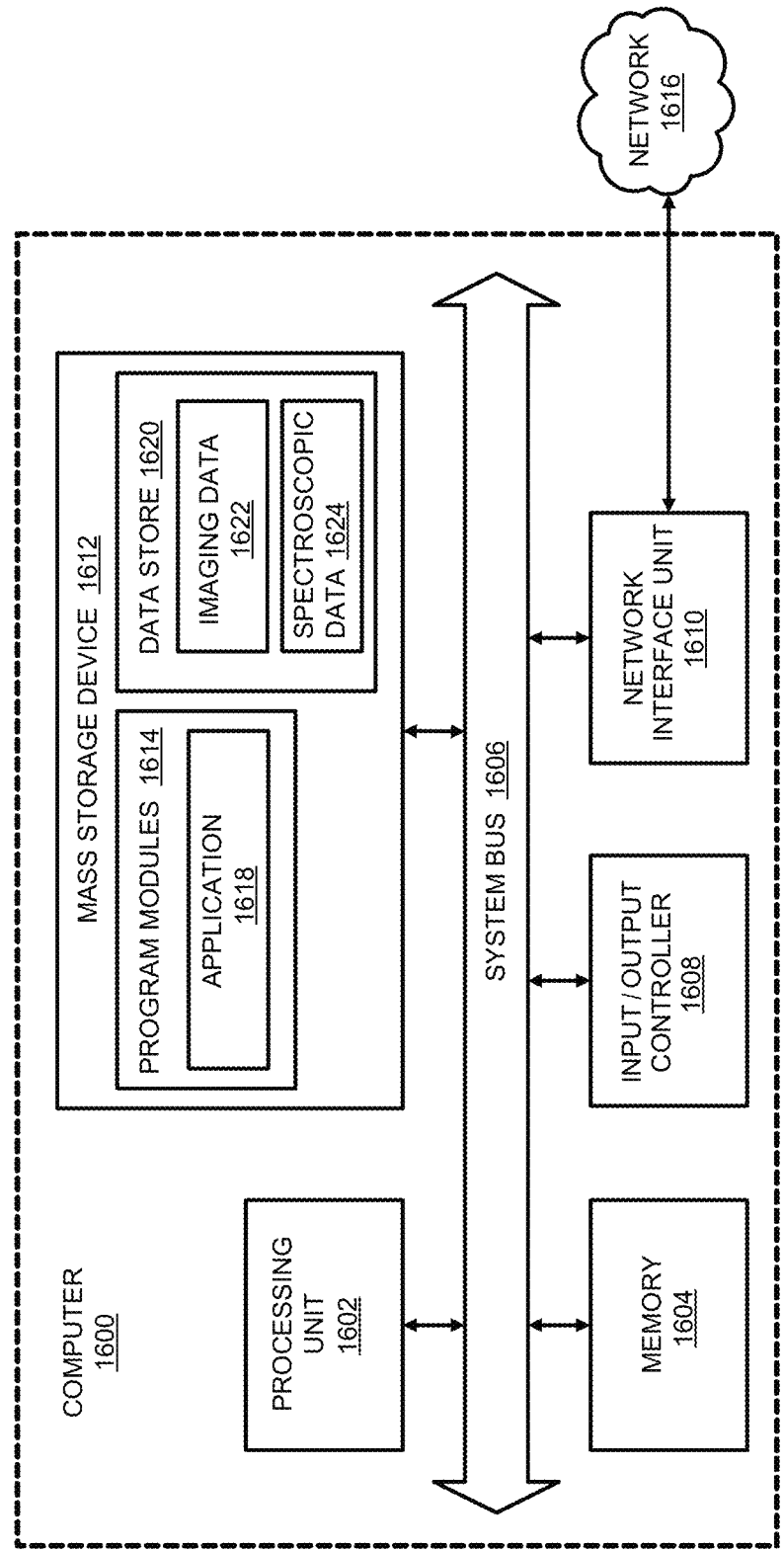

FIG. 16 is a computer architecture diagram showing a general computing system capable of implementing some aspects of the present disclosure in accordance with one or more embodiments.

DETAILED DESCRIPTION

Some aspects of the present disclosure relate to systems and methods for examining a subject. Although example embodiments of the present disclosure are explained in detail herein, it is to be understood that other embodiments are contemplated. Accordingly, it is not intended that the present disclosure be limited in its scope to the details of construction and arrangement of components set forth in the following description or illustrated in the drawings. The present disclosure is capable of other embodiments and of being practiced or carried out in various ways.

It must also be noted that, as used in the specification and the appended claims, the singular forms "a," "an" and "the" include plural referents unless the context clearly dictates otherwise. Ranges may be expressed herein as from "about" or "approximately" one particular value and/or to "about" or "approximately" another particular value. When such a range is expressed, other exemplary embodiments include from the one particular value and/or to the other particular value.

By "comprising" or "containing" or "including" is meant that at least the named compound, element, particle, or method step is present in the composition or article or method, but does not exclude the presence of other compounds, materials, particles, method steps, even if the other such compounds, material, particles, method steps have the same function as what is named.

In describing example embodiments, terminology will be resorted to for the sake of clarity. It is intended that each term contemplates its broadest meaning as understood by those skilled in the art and includes all technical equivalents that operate in a similar manner to accomplish a similar purpose. It is also to be understood that the mention of one or more steps of a method does not preclude the presence of additional method steps or intervening method steps between those steps expressly identified. Steps of a method may be performed in a different order than those described herein without departing from the scope of the present disclosure. Similarly, it is also to be understood that the mention of one or more components in a device or system does not preclude the presence of additional components or intervening components between those components expressly identified.

As discussed herein, a "subject" may be any applicable human, animal, or other organism, living or dead, or other biological or molecular structure or chemical environment, and may relate to particular areas, physiological processes, or components of the subject, for instance specific tissues or fluids of a living subject. It should be recognized that while subjects described in some implementations of various aspects of the present disclosure described herein are biological or chemical in nature, some aspects of the present disclosure may be implemented to examine a variety of non-living subjects, for example rock that is of interest for petroleum exploration, or manufactured objects.

As used herein, "gradient" or "magnetic field gradient" may refer to a spatially varying magnetic field of the type ordinarily used in magnetic resonance imaging (MRI), in which the longitudinal component $B_z$ of the applied magnetic field $\vec{B}$ varies approximately linearly along a certain spatial direction. The gradient $\vec{G}$ may be defined according to:

$$\vec{G} \equiv \frac{dB_z}{dx}\hat{x} + \frac{dB_z}{dy}\hat{y} + \frac{dB_z}{dz}\hat{z}$$

"Gradient pulse" or "magnetic field gradient pulse" as used herein can mean that the amplitude and/or direction of the applied gradient $\vec{G}$ has a time dependence that can be represented by a mathematical function $\vec{G}(t)$. This time variation is assumed to be slow compared to the Larmor frequency of the spins of the tracer at the operating field strength, and may correspond to ramping the gradient amplitude from zero to a desired value, changing from one desired value to another, or ramping the amplitude from a desired value back to zero again. "Static gradient" or "static magnetic field gradient" may also be used when referring to such time-varying magnetic field gradients, even though the amplitude and/or direction of these gradients may not be strictly constant in time, to distinguish them from "RF magnetic field gradients" (see below). Such static gradients can manipulate the orientation of the spins in the transverse plane, without affecting the longitudinal spin component.

"RF gradient" or "RF magnetic field gradient" as used herein can mean a magnetic field $\vec{B}_1$ whose transverse components $B_{1x}$ and/or $B_{1y}$, oscillate in time at or near the Larmor frequency of the spins of the tracer at the operating field strength. The amplitude of this oscillation is not spatially uniform and varies approximately linearly along a specific direction. "RF gradient pulse" or "RF magnetic field gradient pulse" as used herein can mean that the slope and/or direction of this linear variation has a time dependence that is slow compared to the Larmor-frequency oscillations, and may correspond to ramping the slope from zero to a desired value, changing from one desired value to another, or ramping the slope from a desired value back to zero again. Such RF gradients can manipulate the orientation of the spins with respect to the longitudinal axis, thereby altering both transverse and longitudinal spin components, albeit in spatially nonuniform way.

One or more data acquisition or data collection steps as described herein in accordance with one or more embodiments may include acquiring, collecting, receiving, or otherwise obtaining data such as imaging data and spectroscopy data corresponding to a subject. By way of example, data acquisition or collection may include acquiring data via a data acquisition device, receiving data from an on-site or off-site data acquisition device or from another data collection, storage, or processing device. Similarly, data acquisition or data collection devices of systems in accordance with one or more embodiments of the present disclosure may include any device configured to acquire, collect, or otherwise obtain data, or to receive data from a data acquisition device within the system, an independent data acquisition device located on-site or off-site, or another data collection, storage, or processing device.

An overview of some objectives and example embodiments and implementations of the present disclosure will now be provided. In accordance with some embodiments, the present disclosure described herein provides a method to produce one, two and three-dimensional images of a radioactive tracer, without the use of a gamma camera, wherein the radioactive tracer has a nuclear spin greater than ½ and is polarized. Whereas gamma cameras use collimators that generally block more than 99.9% of the incident gamma rays, some embodiments of the present disclosure can produce full 3-D images using detectors with no collimation. The present disclosure, in some embodiments, also provides methods for using polarized nuclear tracers to obtain diagnostic information about a particular biological or molecular environment or process, including but not limited to, those currently available from magnetic resonance techniques, such as changes in spin-relaxation rates and chemical shifts of resonant frequencies. In accordance with some embodiments, a method can be performed by first polarizing or aligning radioactive nuclei, that is, the spins of the radioactive nuclei are preferentially oriented in a specific direction. The polarized radioactive tracers can then be introduced into the subject or environment that will be imaged or otherwise characterized. Next, the tracer can be subjected to pulsed and/or continuous-wave (cw) radio-frequency (RF) electromagnetic fields to manipulate the orientation of the spins. For multi-pixel imaging, the tracer can be subjected to spatially varying magnetic fields (magnetic-field gradients) to encode information about the spatial distribution of the tracer.

The data used to provide diagnostic information and/or imaging information can then be collected by observing time-dependent and/or time-independent count rates in one or more gamma detectors. The data obtained by the gamma detectors can then be processed in order to reconstruct an image of the spatial distribution of the tracer inside the subject and/or a measurement of the magnetic resonance properties of the tracer in the given environment, including but not limited to, spin-relaxation rates and resonance frequencies. The imaging information and/or diagnostic metrics obtained may be used to evaluate and diagnose various biological processes. Examples include, but are not limited to, renal blood flow (RBF), glomerular filtration rate (GFR), blood perfusion in the brain, and pulmonary function. These processes of reconstructing, measuring, evaluation, and diagnosing, among others, can be performed using applications executable by a processor and/or other component of a computer such as the computer 1600 shown in FIG. 16.

As described herein, certain techniques in accordance with some embodiments of the present disclosure that can result in descriptive information that has spatial specificity may generally be referred to as Polarized Nuclear Imaging (PNI). Techniques that can result in descriptive information without spatial specificity, in accordance with some embodiments of the present disclosure may generally be referred to herein as Polarized Nuclear Spectroscopy (PNS). The following provides further detail regarding aspects of the methods described above. Some embodiments of PNI in accordance with the present disclosure can include embodiments in which spectral information is obtained from multiple areas of the subject with well-defined spatial specificity, thereby merging elements of both PNI and PNS.

In some embodiments of the present disclosure, radioactive isotopes with nuclear spin K>½ are polarized or aligned by techniques that can include spin-exchange optical pumping ([2]) or dynamic nuclear polarization (DNP). In one embodiment, the radioactive tracers are isotopes of noble gases such as $^{131m}$Xe. $^{131m}$Xe is used in producing some of the results described herein with reference to certain example implementations, because $^{131m}$Xe is a convenient byproduct of the decay of $^{131}$I, which is widely available. Other possible noble-gases that may be used include $^{129}$Xe, $^{133}$Xe, $^{133m}$Xe, $^{127m}$Xe, and $^{79m}$Kr. In the case of $^{133}$Xe, the isotope first undergoes beta decay transforming into $^{133}$Cs, and some of the time lands in an excited state of $^{133}$Cs, after which the nucleus can emit an 81 keV gamma ray.

Challenges involved in polarizing noble-gas isotopes in accordance with embodiments described herein can he considerably less than is the case when performing MRI using hyperpolarized noble gases because the quantity of noble gas required for PNI or PNS is smaller than that required for hyperpolarized MRI by a factor that may exceed one billion. In contrast to complex techniques employed by past approaches by others ([4]) to polarize $^{129}$Xe, in some embodiments of the present disclosure a straightforward apparatus is used and polarizations are obtained that may be in excess of 50%.

Beyond the use of noble-gas isotopes, PNI and PNS in accordance with some embodiments described herein can also be performed with a wide variety of isotopes that are polarizable using DNP. Oxford Instruments has a "Hypersense DNP Polariser" which uses DNP to polarize isotopes of carbon, nitrogen, silicon and phosphorus. While the Oxford instruments device is currently used exclusively for the polarization of stable isotopes, the device may be adapted in accordance with some embodiments of the present disclosure for radioactive isotopes appropriate for use in PNI and PNS.

Nuclear medicine has established techniques for introducing a tracer to a subject, such as infusing a subject with a radioactive tracer through intravenous injection. Xenon, which is lipophilic, can be dissolved into injectable solutions such as Intralipid (which is approved for human use) and may be injected using similar techniques. Alternatively, $^{131m}$Xe may be inhaled, as is already done in the practice of medicine with $^{133}$Xe during VQ scans, a procedure that is commonly used in large hospitals to diagnose, among other things, pulmonary emboli. As briefly mentioned above, it should be recognized that while some implementations described herein are biological or chemical in nature, a variety of non-living subjects of interest can also be infused with radioactive tracers. Examples include rock that is of interest for petroleum exploration, and manufactured objects being interrogated either for reasons of quality control or to diagnose damage or wear.

In some embodiments of the present disclosure, in a manner that may be analogous to MRI, spatial information can be encoded into the nuclear spins of radioactive tracers using a combination of RF pulses and magnetic-field-gradient pulses. Unlike known nuclear imaging techniques, the spatial information encoded in accordance with embodiments of the present disclosure may be obtained using similar techniques as MRI and thus image resolution similar to MRI, which is much finer than the resolution normally possible with nuclear imaging. When performing MRI, RF is used to tip the nuclear spins such that they are transverse to the direction of the magnetic field. Magnetic field gradients can then be used to obtain sensitivity to different points in "k space", which correspond to different spatial frequencies in the object. The image can then be constructed by taking the Fourier transform of the k-space data. A similar procedure can also be performed in PNI but with a different relationship between the magnetic field gradients and k space. Furthermore, the way in which the k-space data is read out has no direct analogue in MRI. In PNI, the k-space data is read out by observing both time-dependent and time-independent count rates from gamma-ray detectors. Some embodiments described herein concentrate on a scheme in which each point in k space is read out individually, a scheme that in MRI would be referred to as a "fully-phase-encoded pulse sequence." In a variation of this scheme, one could also read out an entire line of k space at one time.

Some embodiments of the present disclosure make it advantageous over MRI in that the quantity of material needed to produce an image is more than a billion-fold less than what is needed in conventional MRI and may provide a multi-order increase in MR sensitivity. Additionally, in some embodiments, unlike MRI, PNI and PNS may be performed at both high and very modest magnetic fields. For example, the proof-of-principle image a) shown in FIG. 12 was obtained using a magnetic field on the order of 10G. Therefore, these advantages may decrease the cost of diagnostics compared to MRI.

It should be recognized that, in some embodiments of the present disclosure, the encoding of spatial information is not required. RF electromagnetic radiation can be used to probe magnetic-resonance (MR) properties of the spins of the radioactive tracer such as spin-relaxation rates ($1/T_1$, $1/T_2$, $1/T_{1\rho}$, $1/T_{2\rho}$, etc.), and shifts in resonance frequencies. These MR properties provide information concerning the environment in which the radioactive tracer finds itself. This allows measurement of MR properties with tiny quantities of materials.

In some embodiments, imaging data are collected multiple times during an imaging sequence. In MRI, the data used to reconstruct the image are gathered by detecting faint radio-frequency electromagnetic (RF EM) radiation using what are essentially antennae. The weak signal size of the RF EM radiation limits magnetic resonance techniques to the detection of a collection of spins that is of the order of perhaps $10^{14}$ to $10^{15}$ in number. In contrast, in some embodiments of the present disclosure, it can be straightforward to detect even a single gamma ray. Aspects of the present disclosure in accordance with some embodiments emphasize the detection of the rate at which gamma rays are detected, and the spatial anisotropies associated with detecting gamma rays in different directions.

As an example, one may be interested in a 30% spatial anisotropy and want to determine it to 10% of itself. For the sake of this example, presume that one wants to determine the rate at which gammas are detected to 10% of itself. Poisson statistics dictates that this would be achieved with the detection of $10^3$ gamma rays over some well-determined length of time.

This is one hundred billion ($10^{11}$) to one trillion times ($10^{12}$) fewer gamma rays than the quantity mentioned earlier that is needed for a good magnetic resonance signal. A more meaningful comparison can be the number of radioactive atoms that would need to be injected into a subject for such a detection. Even taking into account such issues as the branching ratio of the gamma-ray of interest, solid angle, and the fraction of the injected atoms that will undergo decay, the number of atoms required for implementing some embodiments of the present disclosure is on the order of one million, or a billion-fold less than in conventional MR techniques. A comparison may be to compare the number of $^{131m}$Xe atoms that are imaged in FIG. 12 with the number of molecules that would be required to fill the cell with water. About ten billion times more water molecules would be needed compared to the roughly $10^{14}$ $^{131m}$Xe atoms that filled the entire cell.

Certain implementations of the present disclosure therefore enable the use magnetic-resonance techniques with tiny quantities of tracer. As mentioned above, MR properties can be measured that do not necessarily require imaging. Examples include MR resonance spectra which can reveal chemical shifts and spin-relaxation rates. These types of data can be obtained through the observation of gamma rays.

A further detailed description of aspects of the present disclosure will now be provided with reference to the accompanying drawings. The drawings form a part hereof and show, by way of illustration, specific embodiments or examples. In referring to the drawings, like numerals represent like elements throughout the several figures.

Figure 1:
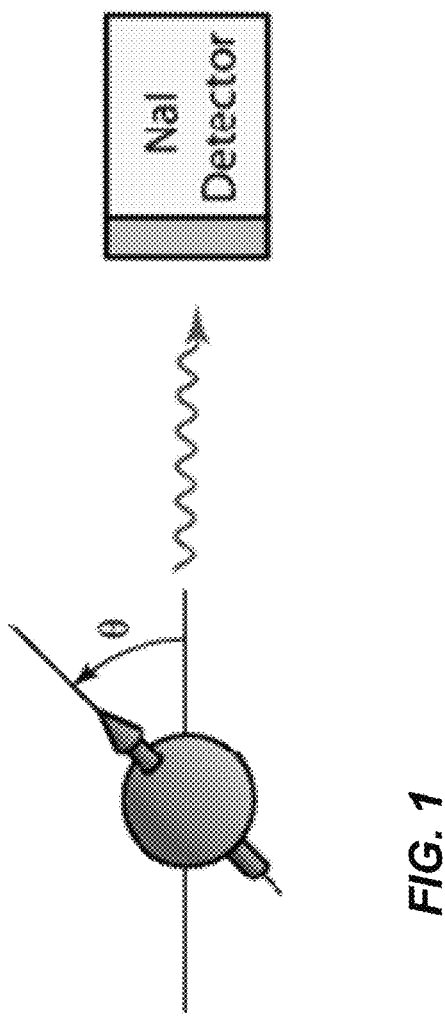
FIG. 1 illustrates a precessing polarized nucleus in which θ is the angle between the polarization direction and the horizontal axis, along which there are two NaI detectors, in accordance with an embodiment of the present disclosure.
Figure 1:
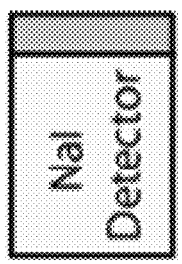

The detection of gamma rays to provide information that can be used to reconstruct an image, in accordance with some embodiments of the present disclosure, will now be described. FIG. 1 depicts a nuclear spin that lies in the plane of the paper making an angle θ with respect to a horizontal axis. If it is assumed that there is a magnetic field perpendicular to the plane of the paper, the spin will precess, and at a time t, the precession angle will be given θ=γBt+θ$_0$, where γ is the gyromagnetic ratio of the nucleus, B is the magnetic field and 90 is the angle the spin makes with respect to the indicated axis at time t=0.

It is established in nuclear physics that the emission of gamma rays from a polarized nucleus is in general spatially anisotropic. As will described in further detail below, the probability that a gamma ray will be emitted at an angle θ with respect to the direction of polarization can be written as $$W(\theta)=\alpha_0+\alpha_2\cos(2\theta)+\alpha_4\cos(4\theta)+ \quad (1)$$

For a fully polarized ensemble of several of the nuclei, the rate of emission at θ=0 has been considered zero. For examples described herein, all but the first two terms in Eq. 1 can be neglected, and the emission rate varies sinusoidally between a minimum at θ=0 and a maximum for $$\theta = \frac{\pi}{2}.$$

The count rate described by Eq. 1 can be compared to the voltage that would be induced in a coil placed at the location of either gamma detector, as would be the case when doing conventional magnetic resonance (MR) measurements. In the case of conventional MR, the voltage would vary between positive and negative maxima, and the frequency of variation would be the Larmor frequency (not twice the Larmor frequency). The count rate observed by the two NaI detectors in FIG. 1 can be used to construct an image in a manner directly analogous to the manner in which EM signals are used in conventional MRI. It may not be possible to orient some of the nuclei in one direction and other nuclei in another direction such that that count rates from the two groups interfere to zero. However, in accordance with some embodiments of the present disclosure, these count rates can be used to reconstruct images, and in ways that have no analogue in MRI.

Steps for using the data from the gamma detection to construct the quantity of interest will now be described. As long as the arrival time of each gamma that is detected can be clearly recorded, count rates, transients, and other features can be reconstructed. In this way, precession frequencies, transients, and even k-space data can all be recovered from the data. When imaging, for example, a multi-dimensional Fourier transform of the k-space data yields the reconstructed image of the object.

The MR properties of water have long been used in the diagnosis of a variety of pathologies, as well as in the characterization of materials in applications such as petroleum exploration. Also, spin-relaxation rates in tumors are well established to differ in certain ways from spin-relaxation rates in healthy tissue. In accordance with some embodiments of the present disclosure, MR properties of polarized radioactive tracers can also be used in a similar manner, but can bring with them important new functionality. Water is ubiquitous in the body, whereas a radioactive tracer is only present once it is introduced. It thus has unique advantages in characterizing processes such as perfusion, and kidney function, among other applications. A tracer making its way from the blood into the kidney's glomeruli, and subsequently though the Bowman's capsules and into the tubules of the nephrons, will experience significantly different chemical environments as it progresses. In a human kidney, the rate of transfer of fluid into the nephrons is approximately 2 cm$^3$/sec. The MR signatures of these different biological compartments can form the basis for a diagnostic modality, in accordance with some embodiments of the present disclosure, that will provide information on physiological functions such as renal blood flow and glomerular filtration rate. Perfusion into any well perfused tissue, including but not limited to kidney, brain, and liver can be monitored through these techniques. Further, the sensitivity to chemical environment according to some aspects of the present disclosure provides for a new type of molecular imaging.

Apparatus

Figure 2:
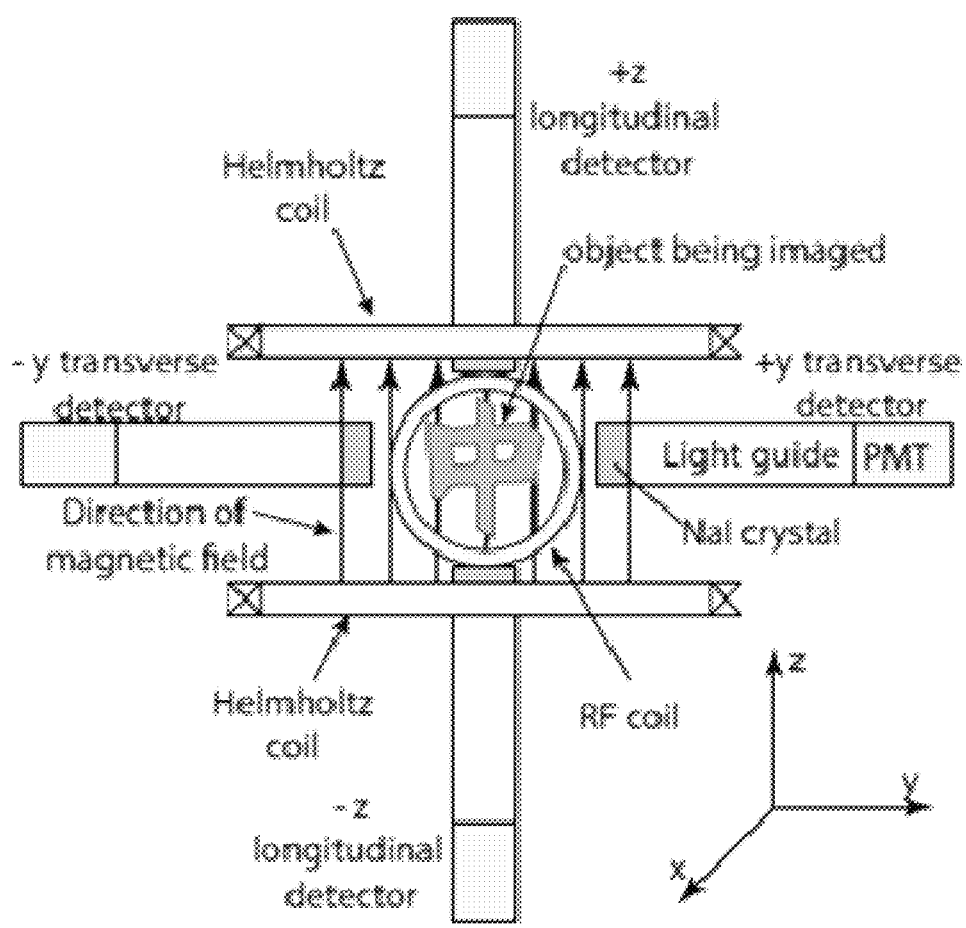
FIG. 2 illustrates a system in accordance with an embodiment of the present disclosure, imaging a subject shown at the center. Four gamma detectors are shown, referenced to the indicated coordinate system. A pair of Hemholtz coils creates a magnetic field in the +z-direction, and the RF coils create an oscillating field along the x-axis. The NaI crystal, Lucite light guide, and photomultiplier tube (PMT) of each gamma detector are each indicated on the +y-detector.

FIG. 2 provides a schematic representation for an apparatus suitable for performing certain aspects of imaging in accordance with some embodiments of the present disclosure. The object to be imaged, in this case a phantom fashioned after the Chinese character for the word "middle", is at the center of the configuration. The detectors labeled −y and +y transverse detector correspond to the two detectors shown in FIG. 1. In one or more imaging implementations, the phantom is subjected to various RF and magnetic-field-gradient pulses followed by the recording of the counts registered by the two detectors. This procedure can be repeated as necessary to obtain the "k-space" data for the image. The Helmholtz coils can provide a modest magnetic field on the order of ten Gauss along the z-direction. The coils used to produce RF are also shown. The coils used to produce magnetic-field gradients are not shown.

Figures 3A, 3B:
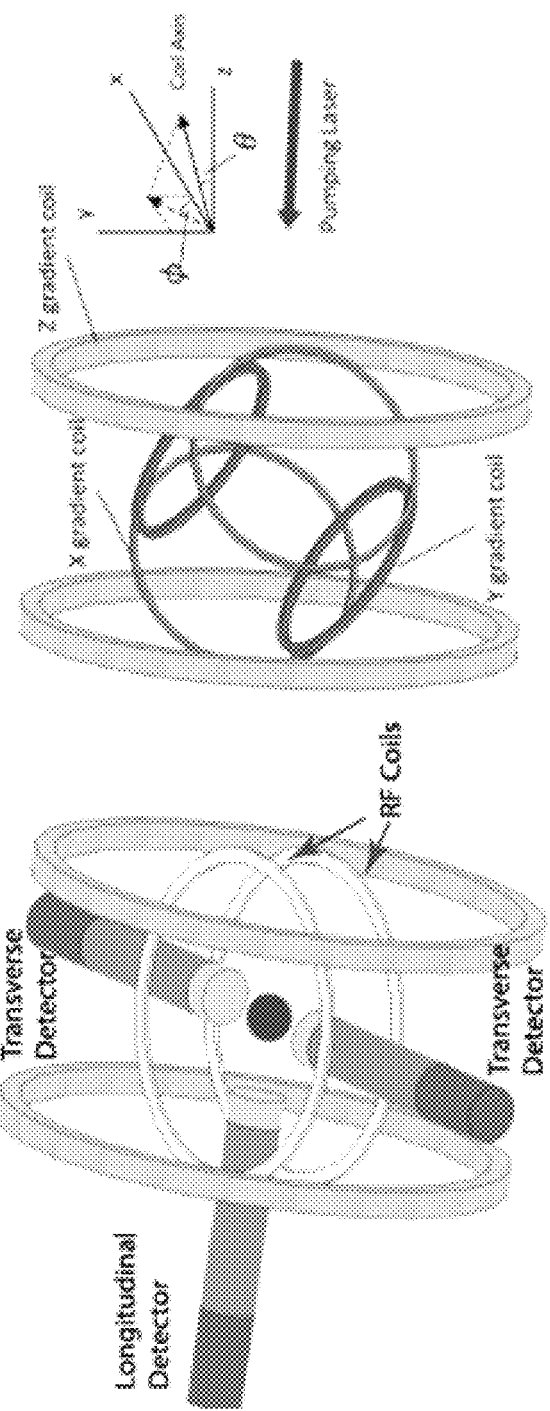
FIGS. 3A and 3B illustrate a pair of Helmholtz coils in accordance with an embodiment of the present disclosure.

FIGS. 3A and 3B schematically show the Helmholtz coils in an embodiment of the present disclosure. The Helmholtz coils may include a holding field (with their symmetry axis along the z-axis), RF coils, with their symmetry axis along the y-axis, and transverse and longitudinal detectors, aligned with the x- and z-axes respectively (FIG. 3A). FIG. 3B shows the gradient coils. The axes of the gradient coils can be oriented at so-called "magic angles" to decouple the x- and y-gradients. A laser beam that can he used for optical pumping is propagated in the z-direction.

Some aspects of the present disclosure described above will now be discussed in further detail, and in particular some aspects of pulse sequences, the acquisition of data from gamma detectors, and the reconstruction of images from that data.

Minimal Fully Phase-Encoded Pulse Sequence

It is established within the context of nuclear physics that nuclear-polarized radioactive isotopes, when emitting a gamma ray, can in general do so in a spatially anisotropic manner. If θ is the angle between the direction of polarization and the direction in which a gamma ray is emitted, the differential probability associated with that angle can be written in terms of a sum over even Legendre polynomials:

$$W(\theta)=1+A_2P_2\cos(2\theta)+A_4P_4\cos(4\theta)+ \quad (2)$$

Here the coefficients $A_k$ can be written $$A_k=\rho_k F_k \quad (3)$$

where $\rho_k$ is an orientation parameter given by $$\rho_k = (2K+1)^{1/2}\sum_m (-1)^{K-m} \times C(KKk; m-m0)a_{m5} \quad (4)$$

where C is the Clebsch-Gordan coefficient and $a_m$ is the normalized population of the magnetic sublevel associated with the quantum number m. The quantities $F_k$ depend on the spins of the initial and final states involved in the gamma decay, as well as the multipolarities of the transitions ([5]). It is Eq. 2 that leads to Eq. 1 given earlier.

The angular dependence given in Eqs. 1 and 2 can be exploited to produce an image in several ways, one of which will now he described. Referring to FIG. 2, it can be assumed for purposes of this example that the spins of the radioactive tracer within the object are polarized in the direction of the magnetic field, along the z-axis. The RF coils can be used to apply a $$\frac{\pi}{2}$$

pulse to the spins, thus rotating them about the x-axis so that they are parallel to the y-axis. The spins have therefore been rotated into the transverse plane. It can next be assumed for purposes of this example that once in the transverse plane, the object is subjected to a pulse of magnetic-field gradients that are characterized by the vector $$\vec{G} = \frac{\partial Bz}{\partial x}\hat{x} + \frac{\partial Bz}{\partial y}\hat{y} + \frac{\partial Bz}{\partial z}\hat{z}.$$

While the magnetic-field gradients can only be fully characterized by a rank-two tensor, in keeping with common practice for much of the MR literature, the other terms will be ignored. The phase of the spins at position r~ within the object being imaged evolves as $\Omega(t, \tau, \vec{r}) = 2\pi\gamma(Bt + \vec{G} \cdot \vec{r}\tau)$, where t is time, $\tau$ is the length of time over which the magnetic-field gradients are applied and $\gamma$ is the gyromagnetic ratio in Hz per Gauss (not radians per Gauss). Substituting our expression for $\Omega(t, \tau, \vec{r},)$ in for $\theta$ in Eq. 1, and integrating over the object being imaged, the count rate measured by the +y transverse detector is given by:

$$R(t) = B\int \rho(\vec{r}) W(\Phi(t, \tau, \vec{r})) d\vec{r} \qquad (5)$$
$$= B\int \rho(\vec{r}) \sum_{m=0,2,4,\ldots} a_m \cos(m\Phi(t, \tau, \vec{r})) d\vec{r}$$

where B depends on the source activity, detector efficiency and the geometry, and can in general be slightly different for different points in the object. For purposes of this example, it can be assumed that B does not vary over the object, is therefore independent of ~r, and can thus be kept outside of the integral. For the special case of $^{131m}$Xe with less than 70% polarization, all terms in Eq. 1 other than those associated with the coefficients $\alpha_0$ and $\alpha_2$ can safely be dropped. For $^{131m}$Xe and the gamma ray being considered, the parameters $\alpha_4$, $\alpha_6$ and $\alpha_8$ (but no higher values of $\alpha_k$) are in general nonzero. Implications of these other terms will be discussed later.

Keeping only the $\alpha_0$ and $\alpha_2$ terms, Eq. 5 can be simplified to:

$$R(t) = B\int \rho(\vec{r})[a_0 + a_2\cos(2\Phi(t, \tau, \vec{r}))] d\vec{r} \qquad (6)$$
$$= B\int \rho(\vec{r})\left[a_0 + a_2\Re\left(e^{i4\pi\gamma \vec{G}\cdot\vec{r}\tau}\right)\right] d\vec{r}$$
$$= B\alpha_0 \int \rho(\vec{r}) d\vec{r} + B\alpha_2 \Re\left(e^{i4\pi\gamma Bt} \int \rho\left(\vec{r}e^{i4\pi\gamma \vec{G}\cdot\vec{r}\tau}\right) d\vec{r}\right)$$

Next, the following is defined, $$R'(t) \equiv \frac{1}{B\alpha_2}\left(R(t) - B\alpha_0 \int \rho(\vec{r}) d\vec{r}\right) \qquad (7)$$

thus finding:

$$R'(t) = \Re\left(e^{i4\pi\gamma Bt} \int \rho(\vec{r}) e^{i4\pi\gamma \vec{G}\cdot\vec{r}\tau} d\vec{r}\right) \qquad (8)$$

Next, the following important definition is made:

$$\vec{k} = 2\gamma \vec{G}\tau \qquad (9)$$

finding:

$$R'(t) = \Re\left(e^{i4\pi\gamma Bt} \int \rho(\vec{r}) e^{i2\pi\vec{k}\cdot\vec{r}} d\vec{r}\right) \qquad (10)$$

From this it can be seen that a Fourier transfrom of R'(t) will have a frequency component at $f_0 = 2\gamma B$ with real and imaginary parts that can be described by a complex function $$A(\vec{k}) = \int \rho(\vec{r}) e^{-i2\pi\vec{k}\cdot\vec{r}} d\vec{r}, \qquad (11)$$

In this imaging scheme, each measurement of the time domain signal R'(t) yields a value of A($\vec{k}$) for a single value of $\vec{k}$. If A($\vec{k}$) is measured over a sufficient set of values of $\vec{k}$, then the object can be reconstructed using the Fourier transform of Eq. 11:

$$\Sigma(\vec{r}) = \int A(\vec{k}) e^{i2\pi\vec{k}\cdot\vec{r}} d\vec{k} \qquad (12)$$

While the derivation above assumes continuous integrals, it is straightforward to extend the argument to discrete sums.

There are several strategies that may be implemented with the minimal fully-phase-encoded pulse sequence for covering the necessary area of k-space. For example, the application of $\pi$ pulses can be used to re-phase the spins and prepare for another point of k-space to be sampled. Also, fast low-angle pulses can be employed to excite only a portion of the tracer at a time. In evaluating such a procedure, it is important to account for the fact that the spins that remain in the longitudinal direction will still be emitting gamma rays. The radioactive tracer can also be replenished with freshly polarized tracer; it should be remembered that any left-over tracer that is unpolarized will contribute to background. For this reason short radioactive-decay half-lives and short biological half-lives are desirable. It should be appreciated that while a fully-phase-encoded imaging scheme is described above, it may in some situations be practical to instead to use an imaging scheme in which one reads a full line of k-space at a time.

During each measurement of a value or line of values in k-space, the gathering of statistics is limited to a time period on the order of the time constant that characterizes the transverse relaxation rate. For low magnetic fields that are well suited to PNI and PNS, transverse relaxation rates due to magnetic field inhomogeneities can be made to be quite small. As will be discussed in further detail below with respect to quadrupole effects, there can also be physics-related contributions to the transverse relaxation rates. One way to obtain a higher count rate is to maximize the solid angle subtended by the detectors. Another is to use a higher level of activity. Averaging can also be used. In some implementations with $^{131m}$Xe, both relatively short transverse relaxation times of ~150 ms were used, as were low levels of activity of a few hundred micro-curies.

Imaging with RF Gradients

In MRI, spatial information associated with the imaged spin density is encoded into the received MR signal by applying linear magnetic field gradients to spins precessing in the transverse plane. The essential mechanism of this encoding is that the application of a linear magnetic field gradient $$\vec{G} \equiv \frac{\partial Bz}{\partial x}\hat{x} + \frac{\partial Bz}{\partial y}\hat{y} + \frac{\partial Bz}{\partial z}\hat{z}$$

along a specific direction creates a linear mapping between precession frequency and spatial position along this direction, during the time that the gradient is being applied. This leads to a Fourier-transform relationship between the frequency spectrum of the received MR signal and the spatial distribution of the spin density. Within the mathematical framework of "k space", the relationship between a spatial frequency $\vec{k}$ and the applied gradient pulse $\vec{G}(t)$ can be written:

$$\vec{k} = \gamma \int \vec{G}(t)dt \quad (13)$$

where $\gamma$ is the gyromagnetic ratio of the nuclear spin expressed in units of Hz/Tesla. If the gyromagnetic ratio were instead expressed in units of radians/Tesla, the relationship would instead be $$2\pi\vec{k} = \gamma \int \vec{G}(t)dt \quad (14)$$

In PNI according to some embodiments of the present disclosure, a similar method can be used to encode spatial information into the measured gamma count rates, with the notable exception that the relationship between the spatial frequency $\vec{k}$ and the applied gradient pulse $\vec{G}(t)$ is given by:

$$\vec{k} = 2\gamma \int \vec{G}(t)dt \quad (15)$$

where $\gamma$ is the gyromagnetic ratio of the nuclear spin expressed in units of Hz/Tesla. This relationship differs by a factor of 2 from MRI case. In PNI it is also possible to use a different method of spatial encoding that is mathematically similar to but fundamentally different from that used in MRI. This method is outlined in the following description.

In the presence of a static longitudinal magnetic field $B_0$ and an RF oscillating transverse magnetic field of the form $B_1 e^{-i\omega_0 t}$, where $B_1$ represents the amplitude of the RF oscillation and $\omega_0 = 2\pi\gamma B_0$ is the Larmor precession frequency of a spin with gyromagnetic ratio $\gamma$ (expressed in units of Hz/Telsa) in a static magnetic field $B_0$, the polar angle $\theta$ between the direction of spin orientation and the positive z axis varies in time according to $\theta(t) = \omega_1 t$, where $\omega_1 = 2\pi\gamma B_1$. If it is further assumed that the amplitude $B_1$ of the RF oscillating field is a linear function of position along a particular direction, such that the spatial variation in the RF field amplitude can be expressed in terms of a gradient $\vec{G}_1$ characterized by $$\vec{G}_1 \equiv \frac{\partial B_1}{\partial x}\hat{x} + \frac{\partial B_1}{\partial y}\hat{y} + \frac{\partial B_1}{\partial z}\hat{z}$$

superimposed on a constant offset $B_1^0$, then the polar angle varies in both position and time according to $\theta(\vec{r}, t) = \omega_1(\vec{r})t = 2\pi\gamma B_1(\vec{r})t = 2\pi\gamma[B_1^0 t + (\vec{G}_1 \cdot \vec{r})t]$.

In many situations of interest, the spatially anisotropic gamma emission probability W from a polarized nuclear tracer depends on the polar angle $\theta$ with respect to the direction of spin orientation according to the expression $W(\theta) = \alpha_0 + \alpha_2 \cos 2\theta$. Thus, with a spatial distribution of spins $\rho(\vec{r})$, all of which are oriented at an angle $\theta$ with respect to the longitudinal axis, then the mean statistical count rate in a longitudinally oriented gamma detector is proportional to $$(\alpha_0 + \alpha_2 \cos 2\theta) \int \rho(\vec{r}) d\vec{r} \quad (16)$$

Further, if the spins in the distribution are exposed to a spatially varying RF magnetic field gradient of the form given above for a time t, then the mean statistical count rate in a longitudinally oriented gamma detector is proportional to $$\int \rho(\vec{r})[\alpha_0 + \alpha_2 \cos(2\theta(\vec{r}, t))]\rho(\vec{r})d\vec{r} \quad (17)$$

This expression is mathematically identical to the expression in Eq. 6 above, and therefore shows that instead of using pulses of static magnetic field gradients to encode information about the spatial distribution of the tracer and reading out this information based on gamma count rates observed in a transverse detector, pulses of RF magnetic field gradients may be used to encode spatial information in a mathematically analogous manner and read out this information based on the count rates observed in a longitudinally oriented detector. Moreover, the fact that in PNI it is natural to perform gamma detection while simultaneously applying RF makes it straightforward to read out imaging data while the RF gradient is being applied, analogous to frequency encoding in the presence of a readout gradient during MRI.

Quadrupole Effects

Common types of MRI derive their signals from the spin- $$\frac{1}{2}$$

nucleus of hydrogen, the proton. There are examples, however, of imaging nuclei with spin greater than $$\frac{1}{2}.$$

In such cases, quadrupole effects can play an important role. The magnetic sublevels can experience shifts the size of which can range from quite small to being so large that the quadrupole shifts result in distinct widely-spaced resonance frequencies. In PNI according to some embodiments of the present disclosure, the observation of a spatial anisotropy in gamma emission necessarily means that the nuclear spin $$K > \frac{1}{2},$$

which can virtually ensure that quadrupole (and higher multiple) interactions play a role at some level.

In one example implementation of the present disclosure, images were produced using $^{131m}$Xe, the nucleus of which has spin and parity of $$\frac{11\,-}{2}$$

and a gyromagnetic ratio of roughly 137.8 Hz/G. It was found that the $$T_2^*$$

of the sample was about 150 milliseconds. A sample of $^{129}$Xe (spin ½), when studied in an apparatus in a nearly identically sized container, had a T2* of around 6 seconds. The gyromagnetic ratio of $^{129}$Xe is 1177.7 Hz/G. Thus, if magnetic field inhomogeneities had been the dominating factor, one could have expected the effective $$T_2^*$$

of $^{131m}$Xe to be around one minute. This difference may be due to quadrupole interactions.

CMZ Pulse Sequences

Cates-Miller-Zheng (CMZ) pulse sequences in accordance with some embodiments of the present disclosure can be used in various ways to generate images and/or spectroscopic information about an ensemble of polarized radioactive nuclei. Unlike MRI, where signal detection relies fundamentally on directly observing time-varying signals from precessing nuclear spins, CMZ pulse sequences do not require observing time-varying signals from precessing spins. Instead, the CMZ imaging pulse sequences provide a method for detecting the real spin moment and the imaginary spin moment of a sample. These moments, defined below, may provide information on the spatial frequencies (k-space data) of the sample that may subsequently be reconstructed into an image. These moments evidence themselves as changes in gamma-detection rates with respect to the rates that would be detected in the absence of nuclear polarization. A method for CMZ imaging pulse sequences may be summarized as follows: 1) applying an RF pulse to tip longitudinal spins into the transverse plane; 2) applying gradient pulses to move around in k-space; and 3) applying additional RF so that the gamma-detection rates in certain detectors provide a measure of the above-mentioned real and imaginary spin moments.

One advantage of CMZ pulse sequences is that the spin-relaxation rates governing the time over which data can be collected are longitudinal relaxation rates instead of transverse relaxation rates. This permits an increase in statistics of roughly two orders of magnitude. In particular, it provides a means to avoid the limits of comparatively fast transverse spin relaxation, making it possible to work with very small quantities of radioactive $^{131m}$Xe.

In variations of the CMZ sequences, nuclear-polarized radioactive isotopes will emit gamma rays in a spatially anisotropic manner. If θ is the angle between the direction of polarization and the direction in which a gamma ray is emitted, the differential probability associated with that angle can be written in terms of a sum over even Legendre polynomials:

$$W(\theta)=1+A_2P_2(\cos 2\theta)+A_4P_4(\cos 4\theta)+\ldots \quad (18)$$

Here the coefficients $A_k$ can be written $$A_k = \rho_k F_k \quad (19)$$

where $\rho_k$ is an orientation parameter given by $$\rho_k = (2K+1)^{1/2} \sum_m (-1)^{K-m} \times C(KKk; m-m0)a_{m5} \quad (20)$$

where C is the Clebsch-Gordan coefficient and $\alpha_m$ is the normalized population of the magnetic sublevel associated with the quantum number m. The quantities $F_k$ depend on the spins of the initial and final states involved in the gamma decay, as well as the multipolarities of the transitions ([5]). It is Eq. 18 that leads to Eq. 1 given earlier.

CMZ Pulse Sequence for PNI with Static Longitudinal Readout

Figure 4:
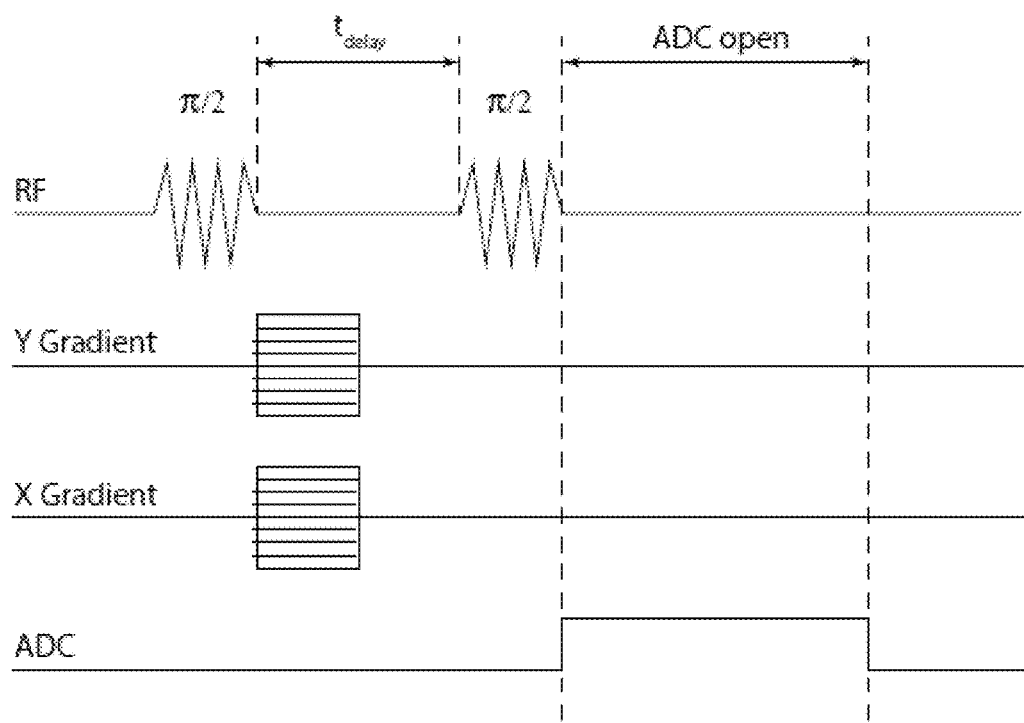
FIG. 4 illustrates a Cates-Miller-Zheng (CMZ) pulse-sequence scheme in accordance with an embodiment of the present disclosure. The spins are first flipped into the transverse plane using a $$\frac{\pi}{2}$$

In some embodiments, the CMZ pulse sequence may have a static longitudinal readout. An example of this variation of the CMZ pulse sequence is illustrated in FIG. 4. The spins are first flipped into the transverse plane using a $$\frac{\pi}{2}$$

pulse, gradient pulses are applied, and then a second $$\frac{\pi}{2}$$

pulse is applied, flipping a subset of the spin back into the longitudinal direction. The ADC is then opened, where the primary signal comes from the two longitudinal detectors.

FIG. 5 illustrates the resulting effect on the spins in the sample according to an embodiment of the present disclosure. Initially, the spins are assumed to be parallel to the z direction, as shown in image a). Next, a $$\frac{\pi}{2}$$

pulse is applied to tip the spins into the transverse (x-y) plane, as shown in image b). The position vector $\vec{r}$ designates the spins associated with a particular location in the sample. The spins are precessed about the z-axis, and the resulting precession angle θ is the result of both the static magnetic holding field, as well as any magnetic-field gradients that are applied, as shown at image c). Finally, after a time, $t_{delay}$, a second $$\frac{\pi}{2}$$

pulse is applied, causing the spins associated with $\vec{r}$ to be rotated into the y-z plane, where they precess in a cone with half-angle θ, as shown at image d). At this point, a data acquisition window is opened and the arrival of gamma rays is recorded as a function of time.

Through the method illustrated in FIG. 5, the gamma detector placed along either the +z or −z directions may observe a count rate corresponding to a time-independent probability of emission. The spins depicted in image d) of FIG. 5 may precess in such a manner that they always maintain a constant angle θ with respect to the z-axis. Given the spatial anisotropy described by Eq. 1, this means that the probability of a photon being emitted along the z-axis remains constant. The spins associated with different parts of the sample, that is, associated with different position vectors $\vec{r}$, may in general be associated with different values of θ; however, once the second $$\frac{\pi}{2}$$

is applied, the angles with respect to the z-axis remain constant. The constant value of the count rate may provide information on each point in k-space.

The following equations provide a mathematical description and definitions for the steps of the method illustrated in FIG. 5 and for reconstructing an image using CMZ pulse sequences, according to an example embodiment. First, it is assumed that the sample is subjected to linear gradients described by the vector $$\vec{G} = \frac{\partial B_z}{\partial x}\hat{x} + \frac{\partial B_z}{\partial y}\hat{y} \quad (21)$$

Assuming the time over which the gradients are applied is given by τ, then the angle θ as shown in image c) in FIG. 5 is given by $$\theta = 2\pi\gamma(\vec{G}\cdot\vec{r}\tau + B_z t) \quad (22)$$

The count rate that will be observed in a longitudinal detector after the second π/2 pulse applied at a time $t = t_{delay}$ can be calculated using the following equations. Let $\tau_{Larmor}$ be the Larmor period of the precessing spins. If $$t_{delay} = n\frac{\tau_{Larmor}}{2} \quad (23)$$

where n is an integer, then using Eq. 1 above, and retaining only the first two terms, the count rate in a detector along the z-axis for a collection of spins at position $\vec{r}$ can be given by $$W(\theta) = a_0 + a_2\cos(2\theta) \quad (24a)$$

$$= a_0 + a_2\cos\left(4\pi\gamma\left(\vec{G}\cdot\vec{r}\tau + B_z n\left(\frac{\tau_{Larmor}}{2}\right)\right)\right) \quad (24b)$$

$$= a_0 + a_2\cos\left[4\pi\gamma\vec{G}\cdot\vec{r}\tau + 2\pi n\right] \quad (24c)$$

$$= a_0 + a_2\cos\left(4\pi\gamma\vec{G}\cdot\vec{r}\tau\right) \quad (24d)$$

Defining $$\vec{k} = 2\gamma\vec{G}\tau \quad (25)$$

$W'_c(\vec{k}, \vec{r})$ can be defined as the count rate corresponding to a particular value of $\vec{k}$, a particular position $\vec{r}$, and the value of $t_{delay}$ given in Eq. 23. Thus, $$W'_c(\vec{k}, \vec{r}) = a_0 + a_2\cos(2\pi\vec{k}\cdot\vec{r}) \quad (26)$$

where the subscript c refers to the fact that with the choice of $t_{delay}$ given in Eq. 23, a cosine on the right-hand side of Eq. 24 and Eq. 26 is computed. Lastly, $W'_c(\vec{k}, \vec{r})$ is integrated over $\vec{r}$ to obtain a quantity of the real spin moment of a sample corresponding to a particular value of $\vec{k}$:

$$S\Re(\vec{k}) = \int\rho(\vec{r})(a_0 + a_2\cos(2\pi\vec{k}\cdot\vec{r}))d^3\vec{r} \quad (27)$$

Next the following value for $t_{delay}$ is considered:

$$t_{delay} = \frac{(n+1/4)\tau_{Larmor}}{2} \quad (28)$$

in which case $$W(\theta) = a_0 + a_2\cos\left[4\pi\gamma\vec{G}\cdot\vec{r}\tau + B_z\frac{(n+1/4)\tau_{Larmor}}{2}\right] \quad (29)$$
$$= a_0 + a_2\cos\left[4\pi\gamma(\vec{G}\cdot\vec{r}\tau + 2\pi n + \frac{\pi}{2}\right]$$

and using the notation introduced earlier $$W'_s(\vec{k}, \vec{r}) = a_0 - a_2\sin(2\pi\vec{k}\cdot\vec{r}) \quad (30)$$

where here the subscript s refers to the fact that with this choice of $t_{delay}$ the sine on the right-hand side of Eqs. 29 and 30 is computed. The imaginary spin moment of a sample corresponding to a particular value of $\vec{k}$ is computed:

$$S_\Im(\vec{k}) = \int\rho(\vec{r})(a_0 - a_2\sin(2\pi\vec{k}\cdot\vec{r}))d^3\vec{r} \quad (31)$$

Next, a complex function $A(\vec{k})$ is considered, defined such that $$\Re_E(A(\vec{k})) \equiv (S\Re(\vec{k}) - \int\rho(\vec{r})a_0 d^3\vec{r})/a_2 = \int\rho(\vec{r})\cos(2\pi\vec{k}\cdot\vec{r})d^3\vec{r} \quad (32)$$

and $$\Im_m(A(\vec{k})) \equiv (S_\Im(\vec{k}) - \int\rho(\vec{r})a_0 d^3\vec{r})/a_2 = \int\rho(\vec{r})\sin(2\pi\vec{k}\cdot\vec{r})d^3\vec{r} \quad (33)$$

From these definitions, up to an offset of $$A_0 = \int\rho(\vec{r})a_0 d^3\vec{r} \quad (34)$$

and a normalization of $a_2$, the real and imaginary spin moments are the real and imaginary parts of the function $A(\vec{k})$. $A(\vec{k})$ can better be written in the form:

$$A(\vec{k}) = \int\rho(\vec{r})e^{-2\pi i\vec{k}\cdot\vec{r}}d^3\vec{r} \quad (35)$$

The spin moments $\Re_E(\vec{k})$ and $\Im_m(\vec{k})$ are both real, measurable count rates, as is the offset $A_0$. By measuring these quantities as a function of $\vec{k}$, $A(\vec{k})$ can be determined. Once measured, the image may be reconstructed by taking the Fourier transform of Eq. 35:

$$\rho(\vec{r}) = \int A(\vec{k})e^{2\pi i\vec{k}\cdot\vec{r}}d^3\vec{k} \quad (36)$$

By measuring the asymmetries between a set of time-independent count rates in gamma detectors, an image may be reconstructed of a subject.

Non-Longitudinal Gamma Detection

In addition to longitudinal detectors, non-longitudinal detectors may be used in some embodiments of the present disclosure. The following mathematical description illustrates the applicability of non-longitudinal detectors.

FIG. 6 illustrates a detector that is placed at an angle $\theta_d$ with respect to the z-axis. A spin is precessing in a cone whose sides make an angle $\theta$ with respect to the (in this case negative) z-axis. The angle between the spin direction and the detector, $\theta_{eff}$, changes with time, thus the count rate in this detector may also change with time, differing from the constant count rate of the longitudinal detector. The time average of the count rate seen by the non-longitudinal detector is computed. The azimuthal angle, $\varphi$ with respect to the x-axis, describes the spin vector's motion as it traces its path along the indicated cone.

First, $$\cos\theta_{eff} = \cos\theta_d \cos\theta + \sin\theta_d \sin\theta \cos\phi \quad (37)$$

where $\theta_{eff}$ represents the (time-dependent) angle between a vector extending from the origin to the detector and a vector pointing in the spin direction. The count rate may have a term proportional to $$\cos 2\theta_{eff} = 2\cos^2\theta_{eff} - 1 \quad (38)$$

$$= 2\left[\begin{array}{c}\cos^2\theta_d\cos^2\theta + 2\cos\theta_d\cos\theta\sin\theta_d\sin\theta\cos\phi + \\ \sin^2\theta_d\sin^2\theta\cos^2\phi\end{array}\right] -$$

The angle is time-dependent, however, as the spins precess about the static field. Averaging over the interval $0 < \varphi < 2\pi$, it is determined that $$\langle\cos(2\theta_{eff})\rangle = \frac{1}{4}\left[-1 + \cos 2\theta_d + (1 + 3\cos(2\theta_d))\cos(2\theta)\right] \quad (39)$$

Eq. 39 can be used to write the rate seen by a detector at angle $\theta_d$ for an ensemble of spins that make an angle $\theta$ with respect to the z-axis as illustrated in FIG. 6:

$$W(\theta, \theta_d) = a_0 + a_2\langle\cos(2\theta_{eff})\rangle \quad (40)$$

$$= a_0 + \left(\frac{a_2}{4}\right)[\cos(2\theta_d) - 1] + \left(\frac{a_2}{4}\right)$$

$$[3\cos(2\theta_d) + 1]\cos(2\theta)$$

The count rate is still sensitive to $\cos(2\theta)$, but the analyzing power has been modified by the factor $$\left(\frac{a_2}{4}\right)$$

[3 $\cos(2\theta_d)$+1]. In fact, at the so called "magic angle" of 54.74°, the analyzing power goes to zero. Eq. 40 can be used to extract imaging information from a detector at an arbitrary angle when using CMZ of the style described above for "*CMZ pulse sequence for PNI with static longitudinal readout*", and can be used for performing CMZ with spin locking as will now be described immediately below.

CMZ Sequence with Spin Locking

In some embodiments of the present disclosure, the pulse sequence described above for "*CMZ pulse sequence for PNI with static longitudinal readout*" may involve the NMR technique of "spin locking". In this approach, the imaging information may be read out from counters placed in the transverse (x-y) plane while the spins are "locked" to the oscillating RF $B_1$ field. This is not possible in conventional MRI since spin locking requires the $B_1$ field to be turned on, and this would normally prevent the detection of the faint electromagnetic signals from the precessing spins, since the RF would be overwhelmingly stronger. In PNI and PNS according to some embodiments of the present disclosure, since gamma rays are being detected, it is quite irrelevant whether or not the RF is on during detection.

As discussed below, CMZ with spin locking can measure both the real and imaginary spin moments defined by Eqs. 27 and 31 but in a different manner. FIG. 7 illustrates the CMZ pulse sequence with spin locking, according to an embodiment of the present disclosure. First, longitudinal spins are rotated into the transverse plane and begin to precess, as seen at a) and b). With the application of magnetic field gradients, the spins corresponding to different locations in the sample precess faster or slower according to the net magnetic field experienced, as shown at c). In c), the spins corresponding to different locations in the sample, that is different values of $\vec{r}$, are shown spreading out into a disk. In c), instead of single values of $\theta$, multiple values of $\theta$, each corresponding to different locations $\vec{r}$ in the object, are shown.

In FIG. 7, d) illustrates a difference between basic CMZ as shown in FIG. 4 and CMZ with spin-locking. As shown, as a result of the RF field being turned on and left on during detection, the motion of the spins is most easily understood in a frame of reference, rotating about the z axis, at the Larmor frequency in the same direction as the precessing spins. In this frame, the effective Hamiltonian describing the system has no static holding field. Thus, the "disk of spins" is simply stationary. When a resonant RF field is switched on, however, the effective Hamiltonian in the rotating frame governing the motion of the spins has the form of a static field wan magnitude $$\frac{B_1}{2},$$

at least to the extent that the counter-rotating field can be ignored. At this point, the disk will begin to precess about the axis defined by the direction of $B_1$. Formally, this is identical to the situation already considered above for "*CMZ pulse sequence for PNI with static longitudinal readout*", when the spins precessed around the static holding field, which is in the z direction. Thus, when using a CMZ sequence with spin locking, the count rate in the $B_1$ direction equals the count rate in the z direction when using a CMZ sequence with static longitudinal readout. To be more specific, it is useful to refer to the motion of the spins in the sample when k=0 (that is, zero gradients). In some embodiments, the CMZ pulse sequence with spin locking may proceed as follows: 1) apply a $$\frac{\pi}{2}$$

pulse, 2) apply gradients to move to a particular point in $\vec{k}$-space, and 3) turn on the RF and begin recording gamma counts.

The count rate that will result may depend on when the RF is turned on. Following the first $$\frac{\pi}{2}$$

pulse, we spins may De pointing along the x-axis. Assuming that $B_1$ will initially be along the y-axis, if the RF is turned on at a time corresponding to when $\vec{k}=0$ spins are also pointing along the y-axis, the count rate in the $B_1$ direction may be given by the definition in Eq. 27 as the real spin moment. If instead the RF is turned on when the $\vec{k}=0$ spins have precessed an additional $$\frac{\pi}{4}$$

radians, the count rate along the $B_1$ direction may be given by what has been defined in Eq. 31 as the imaginary spin moment.

While the preceding analysis tells about a particular direction (that of $B_1$) in the rotating frame, in some embodiments measurements may also be made in the lab frame, where the direction of $B_1$ rotates at the Larmor frequency. To determine the time-dependent count rate in any given detector, the count rate may be calculated as a function of an arbitrary angle with respect to $B_1$. The following derivation utilizes the mathematical description of non-longitudinal detection.

Eq. 40 can be used to express the count rate seen by an individual detector in the transverse (x-y) plane during spin locking. Consider a detector that is placed at the azimuthal angle corresponding to $B_1$ at the moment it is turned on. If $\omega_0 \equiv 2\pi\gamma B_z$, $\theta_d = \omega_0 t$. Substituting this into Eq. 40 and rearranging, $$W(\theta, t) = a_0 + \left(\frac{a_2}{4}\right)[\cos 2\theta - 1] + \left(\frac{a_2}{4}\right)[3\cos 2\theta + 1]\cos(2\omega_0 t) \quad (41)$$

The quantity $\alpha_0$ is the average of the counting rates in the longitudinal and transverse directions when the spins are pointing along the holding field. Next Eq. 41 is expressed in the form $$W(\theta, t) - \alpha_0 = A + B \cos(2\omega_0 t), \quad (42)$$

where A and B are the constant and oscillating terms of the subtracted counting rate $W(\theta, t) - \alpha_0$. It can be recognized that $A + B = \alpha_2 \cos(2\theta)$. Eq. 42 refers to a specific value of $\theta$, which in practice, corresponds to a specific location F within the object being imaged. Next the following to quantity is considered $$\int (A+B)\rho(\vec{r})d^3\vec{r} = \int \alpha_2 \cos(2\theta)\rho(\vec{r})d^3\vec{r}, \quad (43)$$

where $\theta = 2\pi\gamma(\vec{G}\cdot\vec{r}\tau + B_z t)$ as defined previously in Eq. 22. It is thus the case that $$\int (A+B)\rho(\vec{r})d^3\vec{r} = S\Re(\vec{k}) - \alpha_0 \quad (44)$$

where $R_E(\vec{k})$ is the real spin moment defined previously in Eq. 27, assuming a normalization such that the integral of the spin density $\int \rho(\vec{r})d^3\vec{r} = 1$. The corresponding quantity for the imaginary spin moment may be obtained by delaying the time at which $B_1$ is turned on by $$\frac{1}{8}$$

of a Larmor period. Alternatively, $B_1$ may be turned on at the same time but applied in a direction that is 45° different.

While the preceding discussion assumed a detector positioned in the direction of $B_1$ when it is turned on, any detector in the transverse plane may be used by including an appropriate phase to account for Larmor precession. Using Eq. 44 and the corresponding relationship for the imaginary spin moment, the k-space data may be constructed as was done earlier using Eqs. 32 and 33.

CMZ using Rabi Precession

In some embodiments of the present disclosure, CMZ imaging pulse sequences are associated with Rabi Precession Spectroscopy (RPS). CMZ with spin locking differs from CMZ RPS in that the focus is on signals seen by the longitudinal detector rather than the signals seen by the transverse detectors. Similar to the procedure for "*CMZ sequence with spin locking*", described above, CMZ RPS may consist of three main steps: 1) applying an RF pulse to tip longitudinal spins into the transverse plane, 2) applying gradients to move to a particular point in $\vec{k}$-space (although this step may be omitted if not creating a multi-pixel image), and 3) turning on the RF and begin recording gamma counts in the longitudinal detector.

To lowest order, the longitudinal-detector rate may be periodic at twice the Larmor period corresponding to the amplitude of the applied RF field $B_1$. That is, the frequency may be $2\omega_r = 4\pi\gamma B_1$. The amplitude of the oscillating part of the longitudinal-detector rate may carry imaging information in a similar manner to the other embodiments previously described. In addition to the amplitude of the oscillating signal, a distribution of frequencies around the "carrier frequency" of $\omega_r$ may be observed. This distribution reflects chemical shifts of different biological compartments, and even quadrupole interactions with different biological compartments.

As has been the case previously, ensembles of spins from different values of $\vec{r}$ will each acquire a phase $\theta = 2\pi\gamma(\vec{G}\cdot\vec{r}\tau + B_z t)$ as described in Eq. 22. The projection of those spins onto the direction of $B_1$ is the quantity to which we are sensitive with the transverse detectors. The projection of those spins onto the direction perpendicular to $B_1$, however, is the quantity to which we are sensitive with the longitudinal detectors.

In the rotating frame, the disk of spins simply rotates around $B_1$. If $\theta$ is the angle a spin makes with respect to $B_1$, then $$\cos(\theta_{eff}) = \sin(\theta)\sin(\omega_r t) \quad (45)$$

where $\theta_{eff}$ is the angle between the spin and the longitudinal detector. From Eq. 45 it is evident that $$\cos(2\theta_{eff}) = (1-\cos(2\theta))\sin^2(\omega_r t) - 1 \quad (46)$$

and the longitudinal count rate $W_{long}$ is thus given by $$W_{long} = \alpha_0 - \alpha_2 + \alpha_2(1-\cos(2\theta))\sin^2(\omega_r t). \quad (47)$$

expressing $$W_{long} = A + B\sin^2(\omega_r t), \quad (48)$$

it then follows that $$S\mathcal{R}(\vec{k}) - \alpha_0 = \alpha_2 \cdot B, \qquad (49)$$

and a corresponding quantity for $S_{\Im}(\vec{k})-\alpha_0$ can also be constructed. So once again, a measurable quantity may be computed to relate back to the k-space data discussed previously. Since the time scales with which the longitudinal detector can be sampled may be on the order of tens of seconds, frequencies differing from the central frequency by as little as several mHz may be detected under the right conditions.

Molecular Imaging with PNI RPS

The method summarized by Eqs. 45-49 provides an unambiguous probe of the chemical environment experienced by the polarized radioactive tracer. The method may be used with or without spatial specificity such that it may be capable of non-imaging application, such as a kidney-specific diagnostic since the kidneys in a human are spatially separated by sufficient distance. The fact that RPS can be used in an imaging or non-imaging fashion provides considerable flexibility. A non-imaging sequence could be accomplished with a simpler apparatus with smaller radiation dose to the subject. With a larger quantity of tracer, however, and the ability to apply magnetic-field gradients, sophisticated molecular-imaging procedures can be developed.

CMZ Pulse Sequence for PNS with Static Longitudinal Readout

In some embodiments of the present disclosure, CMZ pulse sequences may be used to extract spectral information that does not require direct observation of time-varying signals from spins in the transverse plane. A pulse sequence may be used that is nearly identical to the imaging pulse sequence for "CMZ pulse sequence for PNI with static longitudinal readout" described above, except that no gradients are applied during the "mixing" time between the first and second RF pulses. Instead of measuring the count rates for different gradient moments, the count rates are measured for different mixing times. This information may then be used to determine the frequency spectrum of the spins, such as would originate from different chemical shifts or field inhomogeneities.

The following method may be used, according to an embodiment of the present disclosure. Initially, the spins may be assumed to be parallel to the z direction. Next, a $$\frac{\pi}{2}$$

pulse may be applied about some axis perpendicular to the z direction to tip the spins into the transverse (x-y) plane. It may be assumed that the RF pulse is applied about the y axis. Next, the spins associated with a particular Larmor precession frequency $\omega=\gamma B_z$ may be considered. This frequency may depend on both the gyromagnetic ratio $\gamma$ of the nucleus and the local magnetic field $B_z$. The spins then may precess about the z axis, and the resulting precession angle θ may evolve with time according to θ=ωt. Finally, after a time t', a second $$\frac{\pi}{2}$$

pulse may be applied about the y axis, causing the spins associated with the precession frequency ω, which now have precession angle θ=ωt' to be rotated into the y-z plane, where they will begin precessing about the z-axis in a cone with half-angle θ. At this point a data acquisition window may be opened and the arrival of gamma rays may be recorded as a function of time.

The count rate that may be observed by a gamma detector placed along either the +z or −z directions may be determined as follows. The spins depicted in d) of FIG. 5 may precess in such a manner that they always maintain a constant angle θ with respect to the z-axis. Given the spatial anisotropy described by Eq. 1, the probability of a photon being emitted along the z-axis remains constant. The spins associated with different frequencies in the sample (generally due to chemical shifts and/or magnetic field inhomogeneity) are associated with different values of θ. Once the second $$\frac{\pi}{2}$$

is applied, their angles with respect to the z-axis remain constant. Similar to the imaging case considered above in "CMZ pulse sequence for PNI with static longitudinal readout", the constant value of the count rate provides information on each point in the time domain. This is quite distinct from conventional NMR spectroscopy in which one always detects a time-varying signal.

Once again Eq. 1 is used and only the first two terms are kept. After the second $$\frac{\pi}{2}$$

pulse is applied at time t', the count rate in the longitudinal detector corresponding to a given precession frequency ω is proportional to $$W_0(\theta) = \alpha_0 + \alpha_2 \cos(2\theta) = \alpha_0 + \alpha_2 \cos(2\omega t') \qquad (50)$$

Integrating $W_0$ over all spins in the sample, the total count rate in the longitudinal detector is proportional to $$S\mathcal{R}(t') = \int \rho(\omega)[\alpha_0 + \alpha_2 \cos(2\omega t')]d\omega \qquad (51)$$

where $\rho(\omega)$ represents the spectral density of spins in the sample. By repeating this measurement for a range of delay times t', the Fourier relationship between ω and t' that provides a measure of the frequency spectrum $\rho(\omega)$ can be constructed.

Moreover, a complex-valued Fourier spectrum may be constructed by further repeating the measurements outlined above but applying the second RF pulse about a different axis in the transverse plane that is oriented at 45° with respect to the y-axis. In this case, the count rate in the longitudinal detector corresponding to a given precession frequency ω is proportional to $$W_{45}(\theta) = \alpha_0 + \alpha_2 \cos(2(\theta - \pi/4)) = \alpha_0 + \alpha_2 \sin(2\theta) = \alpha_0 + \alpha_2 \sin(2\omega t') \qquad (52)$$

Integrating $W_{45}$ over all spins in the sample, the total count rate in the longitudinal detector is proportional to $$S_{\Im}(t') = \int \rho(\omega)[\alpha_0 + \alpha_2 \sin 2\omega t']d\omega \qquad (53)$$

Finally, the complex function A(t') is considered, defined such that $$\mathfrak{R}_E(A(t')) \equiv (S\mathfrak{R}(t') - \int \rho(\omega)\alpha_0 d_\omega)/\alpha_2 = \int \rho(\omega)\cos(2\omega t') d\omega \quad (54)$$

and $$\mathfrak{I}_m(A(t')) \equiv (S_\mathfrak{I}(t') - \int \rho(\omega)\alpha_0 d\omega)/\alpha_2 = \int \rho(\omega)\sin(2\omega t') d\omega \quad (55)$$

From these definitions, up to an offset of $$A_0 \equiv \int \rho(\omega)\alpha_0 d\omega \quad (56)$$

and a normalization of $\alpha_2$, the real and imaginary spin moments are the real and imaginary parts of the function A(t'). A(t') can be written in the form:

$$A(t') = \int \rho(\omega) e^{i\omega t'} d\omega \quad (57)$$

The quantities $S\mathfrak{R}(t')$ and $S_\mathfrak{I}(t')$ are both real measurable count rates, as is the offset $A_0$. By measuring these quantities as a function of t', A(t') can be determined. Once measured, the frequency spectrum can be constructed by taking the Fourier transform of Eq. 57:

$$\rho(\omega) = \int A(t') e^{-i\omega t'} dt' \quad (58)$$

By measuring the asymmetries between a set of time-independent count rates in the gamma detectors, a complex frequency spectrum of a sample can be reconstructed.

FIG. 15 is a flow diagram illustrating operations of a method 1500 for examining a subject, according to one embodiment of the present disclosure. As shown, at 1502, nuclei of a radioactive substance are polarized such that the spins of the nuclei are oriented in a specific direction, to generate a polarized radioactive tracer with anisotropic gamma ray emission probability. At 1504, the tracer is introduced into the subject. At 1506, radio frequency oscillating (RF) magnetic fields and/or spatially varying magnetic fields are applied to the tracer, which are configured to manipulate the orientation of the spins such as to manipulate the directional dependence of gamma ray emission from the tracer. At 1508, gamma rays from the gamma ray emission are detected. At 1510, imaging data and/or spectroscopic data associated with the tracer are obtained, based on the detected gamma rays and properties associated with the anisotropic gamma ray emission.

FIG. 16 is a computer architecture diagram showing a general computing system capable of implementing aspects of the present disclosure in accordance with one or more embodiments described herein. A computer 1600 may be configured to perform one or more functions associated with embodiments illustrated in one or more of FIGS. 1-15. For example, the computer 1600 may be configured to perform operations of the method shown in FIG. 15. One or more components of the computer 1600 may be operatively coupled to the systems and apparatus shown in FIGS. 1-3. It should be appreciated that the computer 1600 may be implemented within a single computing device or a computing system formed with multiple connected computing devices. The computer 1600 may be configured to perform various distributed computing tasks, in which processing and/or storage resources may be distributed among the multiple devices.

As shown, the computer 1600 includes a processing unit 1602 ("CPU"), a system memory 1604, and a system bus 1606 that couples the memory 1604 to the CPU 1602. The computer 1600 further includes a mass storage device 1612 for storing program modules 1614. The program modules 1614 may be operable to perform functions associated with embodiments illustrated in one or more of FIGS. 1-15 discussed above, for example to cause the computer 1600 to perform operations of the method shown in FIG. 15. The program modules 1614 may include an application 1618 for performing functions for obtaining and processing data, for example to obtain and process imaging and/or spectroscopic data associated with a subject, as described herein in accordance with various embodiments of the present disclosure. The computer 1600 may be configured to control one or more components of the systems of FIGS. 1-3. For example, the computer 1600 may be configured to control the various components used for polarization of nuclei, application of RF magnetic fields and/or spatially varying magnetic fields, detection of gamma rays, and obtaining and/or processing imaging data and/or spectroscopic data in accordance with embodiments of the present disclosure described herein.

The computer 1600 can be configured to process data obtained by the gamma detector(s) in order to reconstruct an image of the spatial distribution of the tracer inside the subject and/or perform measurements of magnetic resonance properties of the tracer in the given environment, and the computer 1600 can be configured to, based on the obtained data, evaluate and diagnose various biological, chemical, or other processes or conditions of a subject. The computer 1600 can include a data store 1620 for storing data that may include obtained imaging data 1622 and/or spectroscopic data 1624.

The mass storage device 1612 is connected to the CPU 1602 through a mass storage controller (not shown) connected to the bus 1606. The mass storage device 1612 and its associated computer-storage media provide non-volatile storage for the computer 1600. Although the description of computer-storage media contained herein refers to a mass storage device, such as a hard disk or CD-ROM drive, it should be appreciated by those skilled in the art that computer-storage media can be any available computer storage media that can be accessed by the computer 1600.

By way of example and not limitation, computer storage media (also referred to herein as "computer-readable storage medium" or "computer-readable storage media") may include volatile and non-volatile, removable and non-removable media implemented in any method or technology for storage of information such as computer-storage instructions, data structures, program modules, or other data. For example, computer storage media includes, but is not limited to, RAM, ROM, EPROM, EEPROM, flash memory or other solid state memory technology, CD-ROM, digital versatile disks ("DVD"), HD-DVD, BLU-RAY, or other optical storage, magnetic cassettes, magnetic tape, magnetic disk storage or other magnetic storage devices, or any other medium which can be used to store the desired information and which can be accessed by the computer 1600. "Computer storage media", "computer-readable storage medium" or "computer-readable storage media" as described herein do not include transitory signals.

According to various embodiments, the computer 1600 may operate in a networked environment using connections to other local or remote computers through a network 1616 via a network interface unit 1610 connected to the bus 1606. The network interface unit 1610 may facilitate connection of the computing device inputs and outputs to one or more suitable networks and/or connections such as a local area network (LAN), a wide area network (WAN), the Internet, a cellular network, a radio frequency (RF) network, a Bluetooth-enabled network, a Wi-Fi enabled network, a satellite-based network, or other wired and/or wireless networks for communication with external devices and/or systems. The computer 1600 may also include an input/output controller 1608 for receiving and processing input from any of a number of input devices. Input devices may include one or more of keyboards, mice, stylus, touchscreens, microphones, audio capturing devices, and image/video capturing devices. An end user may utilize the input devices to interact with a user interface, for example a graphical user interface, for managing various functions performed by the computer 1600.

The bus 1606 may enable the processing unit 1602 to read code and/or data to/from the mass storage device 1612 or other computer-storage media. The computer-storage media may represent apparatus in the form of storage elements that are implemented using any suitable technology, including but not limited to semiconductors, magnetic materials, optics, or the like. The computer-storage media may represent memory components, whether characterized as RAM, ROM, flash, or other types of technology. The computer storage media may also represent secondary storage, whether implemented as hard drives or otherwise. Hard drive implementations may be characterized as solid state, or may include rotating media storing magnetically-encoded information. The program modules 1614, which include the application 1618, may include instructions that, when loaded into the processing unit 1602 and executed, cause the computer 1600 to provide functions associated with one or more embodiments illustrated in FIGS. 1-15. The program modules 1614 may also provide various tools or techniques by which the computer 1600 may participate within the overall systems or operating environments using the components, flows, and data structures discussed throughout this description.

In general, the program modules 1614 may, when loaded into the processing unit 1602 and executed, transform the processing unit 1602 and the overall computer 1600 from a general-purpose computing system into a special-purpose computing system. The processing unit 1602 may be constructed from any number of transistors or other discrete circuit elements, which may individually or collectively assume any number of states. More specifically, the processing unit 1602 may operate as a finite-state machine, in response to executable instructions contained within the program modules 1614. These computer-executable instructions may transform the processing unit 1602 by specifying how the processing unit 1602 transitions between states, thereby transforming the transistors or other discrete hardware elements constituting the processing unit 1602.

Encoding the program modules 1614 may also transform the physical structure of the computer-storage media. The specific transformation of physical structure may depend on various factors, in different implementations of this description. Examples of such factors may include, but are not limited to the technology used to implement the computer-storage media, whether the computer storage media are characterized as primary or secondary storage, and the like. For example, if the computer storage media are implemented as semiconductor-based memory, the program modules 1614 may transform the physical state of the semiconductor memory, when the software is encoded therein. For example, the program modules 1614 may transform the state of transistors, capacitors, or other discrete circuit elements constituting the semiconductor memory. As another example, the computer storage media may be implemented using magnetic or optical technology. In such implementations, the program modules 1614 may transform the physical state of magnetic or optical media, when the software is encoded therein. These transformations may include altering the magnetic characteristics of particular locations within given magnetic media. These transformations may also include altering the physical features or characteristics of particular locations within given optical media, to change the optical characteristics of those locations. Other transformations of physical media are possible without departing from the scope of the present description, with the foregoing examples provided only to facilitate this discussion.

The following description provides a further discussion of certain aspects of the present disclosure in accordance with example embodiments. A description of example implementations and results of practicing various aspects of the present disclosure will be presented.

EXAMPLE IMPLEMENTATIONS AND RESULTS

Various aspects of the present disclosure may be still more fully understood from the following description of some example implementations and corresponding results and the images of FIGS. 8-14. Some experimental data are presented herein for purposes of illustration and should not be construed as limiting the scope of the present disclosure in any way or excluding any alternative or additional embodiments.

EXAMPLE 1

A first example (hereinafter referred to as "EXAMPLE 1") of practicing aspects of the present disclosure will now be described along with corresponding results and with reference to illustrations in FIG. 8 and FIG. 9. According to this EXAMPLE, samples of $^{131m}$Xe were polarized, a $$\frac{\pi}{2}$$

pulse was applied, and the precessing nuclei were observed solely through the observation of gamma rays. This example of pulse NMR with gamma detection is referred to herein as Polarized Nuclear Spectroscopy (PNS). The result of this study, performed with a small sample of $^{131m}$Xe under sub-optimal conditions, is shown in FIG. 8. In particular, FIG. 8 shows the Fourier transform of the signals from the two gamma detectors in the transverse plane (see FIG. 2) following a $$\frac{\pi}{2}$$

pulse. A peak corresponding to twice the Larmor frequency of $^{131m}$Xe can be clearly seen at the expected frequency.

Now referring specifically to FIG. 9 a subsequent and related study, with higher statistics, used the time domain signal from the gamma detectors, essentially a histogram of counts versus time, which was mixed down to a lower frequency to produce a classic free-induction-decay (FID). While this plot represents multiple averages, the limited statistics are clearly apparent, due in large part to the short effective $T_2$. In particular, FIG. 9 shows a free induction decay obtained by PNS of $^{131m}$Xe, made by mixing down to a lower frequency. The effective $T_2$ is limited by quadropole interactions.

EXAMPLE 2

A second example (hereinafter referred to as "EXAMPLE 2") of practicing aspects of the present disclosure will now be described along with corresponding results and with reference to the illustration in FIG. 10. This EXAMPLE describes other techniques which can be used to observe the motion of the precessing spins of a polarized sample of $^{131m}$Xe (for example the polarized sample from EXAMPLE 1) for longer time scales. One such technique uses spin locking, in which the spins are rotated to the transverse plane using a $$\frac{\pi}{2}$$

pulse, and subsequently, RF is turned back on, and left on, such that the rotating magnetic field of the RF is aligned with the spins. In this situation, the decay is governed by the longitudinal relaxation time in the rotating frame, or $T_{1\rho}$. FIG. 10 shows a sample of $^{131m}$Xe precessing while "spin locked" in the transverse plane. It can be seen that $T_{1\rho}$ is much longer than the effective $T_2$ shown in FIG. 9, approximately 5.2 seconds when the signal is fit with an exponentially damped sinusoid.

EXAMPLE 3

As a third example (hereinafter referred to as "EXAMPLE 3") of practicing aspects of the present disclosure, FIG. 11 shows a frequency spectrum obtained from a sample of hyperpolarized $^{131m}$Xe using Rabi Precession Spectroscopy. A single frequency peak is evident, corresponding to 2ωr at the applied B1 field strength of 0.2 G.

EXAMPLE 4

A fourth example (hereinafter referred to as "EXAMPLE 4") of practicing aspects of the present disclosure will now be described along with corresponding results and with reference to FIGS. 12-14. In FIG. 12, a) illustrates a proof-of-principle image of a glass phantom shaped like the Chinese character for "middle" using the system and apparatus disclosed and b) is a photograph of the phantom. The phantom is a sealed glass cell containing between 1 and 2 mCi of $^{131m}$Xe, around 100 T of $N_2$ and about ten of Torr of $H_2$. The image comprises 32 by 32 pixels in the x-y plane with no slice selection in the z-direction, and is interpolated to 64 by 64 pixels for display. The initial pixel size is 3 mm by 3 mm (or 1.5 mm by 1.5 mm after interpolation).

FIG. 13 shows graphical representations of several sets of measurements that monitor the precession of polarized $^{131m}$Xe. In a), a free-induction decay of $^{131m}$Xe using only gamma-ray detection is shown. In b), counts versus time in the transverse detectors during Rabi oscillations are shown, where data was processed and mixed to a lower frequency to emphasize the oscillations, according to an example embodiment of the present disclosure. In c), the Fourier transform of counts versus time in the longitudinal detector is shown before modulation.

FIG. 14 shows directional-emission-probability distributions of 164 keV gamma rays from $^{131m}$Xe nuclei, according to an embodiment of the present disclosure. In a), a polar plot of Eq. 1 (above) as a function of the angle $\theta_r$ with respect to the direction of orientation (red arrow) is shown for an ensemble of nuclei with polarization of 0% (black line), 70% (dotted blue line), and 100% (solid blue line) respectively. In b), a 3D representation of Eq. 1 for 100% polarized $^{131m}$Xe nuclei oriented along an applied magnetic field B is shown. In c), the directional emission probability of 100% polarized $^{131m}$Xe nucleus oriented in the transverse (x-y) plane is shown. The probability distribution, and the spins, rotate about the z-axis at the Larmor frequency $\omega_L = \gamma B$; the count rate is maximum in the longitudinal detector and oscillates between minimum and maximum in the transverse detector with a frequency of 2ω.

Experimental Setup

The experimental apparatus made use of key components of an existing very-low-field MRI system that has been described previously ([6]). As is the case in the work presented here, the work in reference [6] involved the study of gaseous samples of Xenon, in sealed glass cells, that were polarized using the technique of spin-exchange optical pumping. In the present work, however, the acquisition of imaging data employed three gamma detectors (see also FIG. 3A). Accordingly, those aspects of the apparatus from reference [6] that were used to detect RF signals were not needed. Importantly, the quantity of $^{131m}$Xe atoms contained in the sealed glass phantoms was smaller by a factor of roughly $10^7$ compared with the number of $^{129}$Xe atoms imaged in reference [6].

The three gamma detectors each consisted of three parts: a NaI crystal, a Lucite light guide and a photomultiplier tube (PMT) (see also FIG. 2). The NaI crystals were placed about ~13 cm from the sample and were either 2 or 3 inches in diameter (various combinations were used for the different results presented). The NaI crystals were coupled to the PMTs by light guides with a length of approximately 1 meter, which kept the sensitive PMTs outside of the 0.7 mT holding field, and also insured that magnetic field inhomogeneities caused by the magnetic shielding of the PMTs was well away from the sample being studied. The output signal from each PMT was first fed to a shaping amplifier using a time constant of 0.25 µs. The output of the shaping amplifier was sent to a single channel analyzer (SCA) set with a peak-height window acceptance such that the 164 keV gamma rays from the $^{131m}$Xe were accepted, and background, most of which was due to ≈30 keV X-rays, was largely rejected. The output of the SCA generated a TTL pulse which was then sent to a gate/delay generator to trigger a second TTL pulse with an adjustable width which was set at 3 µs. A National Instruments data acquisition (DAQ) card recorded the output of the gate/delay generator from each of three detectors using three separate input channels as a function of time. The data sampling frequency was set to the inverse of the pulse duration. For example, a sampling frequency of 333 kHz was used for 3 µs wide pulses. Under typical operating conditions, the photon arrival rate was very low compared with the data sampling rate. As a result, most of the time bins were zero. Only a small fraction of the time bins were registered as "1"s when pulses were generated by the gate/delay generators Sample Preparation The $^{131m}$Xe used in the studies was the decay product of commercially available $^{131}$I. It was received in vials, roughly 10 cm$^3$ in volume, which in addition to the $^{131m}$Xe contained a largely unknown mixture of carrier gases, most likely $N_2$, at a pressure of roughly 1 atm. The gas contained in the vial was withdrawn into a syringe and subsequently injected through a rubber septum into a small glass manifold attached to which was both an expandable bladder and a temporary valved holding cell containing a few droplets of Rb. The valve on the holding cell was initially closed, and with the holding cell cooled to liquid nitrogen temperatures, the valve was opened, drawing most of the gas into the holding cell where the $^{131m}$Xe subsequently condensed. The holding cell was then allowed to warm up to room temperature and sit for several hours, thus allowing the Rb to getter components of the carrier gas such as oxygen and water. After several hours, the $^{131m}$Xe was then transferred into a second cell that served as the phantom used for the studies. The second transfer also provided an opportunity to further remove unwanted gasses from the mixture. The fully prepared sample typically contained a few droplets of Rb, 100 to 200 Torr of N$_2$ and about 10 Ton of H$_2$. Nitrogen was needed to aid the optical pumping process. The small amount of H$_2$ caused RbH to form on the cell's interior wall, and has been shown to reduce nuclear spin relaxation in samples of (nonradioactive) $^{131}$Xe$^2$, presumably reducing quadrupole interactions. Care was taken throughout this procedure to avoid releasing more than trace quantities of $^{131m}$Xe into the atmosphere, and those releases were largely confined to a fume hood approved for use with radioactive isotopes. The final sample cell typically contained between a few hundred μCi to about 1.5 mCi of $^{131m}$Xe.

Methods for Non-Imaging Studies

Before imaging, several sets of measurements were performed in which transverse detectors were used to monitor the precession of the polarized $^{131m}$Xe spins about the magnetic holding field. A magnetic holding field of 0.7 mT was used for all studies, which corresponds to a Larmor frequency of about 0.96 kHz for $^{131m}$Xe. At the $^{131m}$Xe polarization levels used, terms in Eq. 1 (above) higher than a$_2$ were negligible, so the oscillations in the gamma-ray detection rates had a frequency of around 1.92 kHz (twice the Larmor frequency) and were readily observed with our data sampling rate of 333 kHz.

To monitor the polarization of the $^{131m}$Xe during SEOP, the asymmetry between the longitudinal and transverse detectors was measured, which can be roughly approximated by the functional form $1-e^{-t/\tau}$ with τ~35 s (with a spin 1

$$\frac{1}{2}$$

nucleus, the actual functional form is considerably more complicated). As a compromise between maximizing polarization and being efficient with our acquisition of data, the sample was polarized for ~100 s prior to each measurement, at the end of which the necessary RF pulses were applied and the data were acquired. The transverse detectors for the FID and spin locking measurements were used, and the longitudinal detector for the Rabi precession measurement.

All of these studies were performed using quantities of $^{131m}$Xe that were around 100 times smaller than would be appropriate for in vitro studies. Furthermore, the non-imaging studies were performed after the samples had decayed substantially from the initial activity levels because, upon receiving a sample of $^{131m}$Xe, the imaging studies were performed first, which were more demanding in terms of statistics. For these reasons, averaging was critical for obtaining the data shown in FIG. 13. For the FID measurement shown in a) of FIG. 13, the $^{131}$mXe polarization was ~55%, the 164 keV gamma count rate was ~1.8 kHz, and ~1300 averages were acquired. For the spin locking measurement shown in b) of FIG. 13, the $^{131m}$Xe polarization was ~55%, the gamma count rate was ~0.8 kHz, and ~400 averages were acquired. For the Rabi precession measurements, the $^{131m}$Xe polarization was ~66%, the count rate was ~4.6 kHz, and ~750 averages were acquired. All the count rates quoted here were measured when $^{131m}$Xe was not polarized. It is worth noting that if a quantity of 100 mCi of $^{131m}$Xe were used (which would result in a radiation dose to a living subject of a few hundred mRem), and two detectors were used instead of one, a count rate of around 2.8 MHz would be achieved. Under these conditions, the statistics shown in c) of FIG. 13 could be achieved in a single measurement with no averages.

Methods for Polarized Nuclear Imaging

The phantom was made of Pyrex glass in the shape of the Chinese character for "middle", and was roughly 6.5 cm by 5.5 cm in size. The phantom was imaged using the pulse sequence illustrated in FIG. 4 and described in detail in the previous section. The image was a 2D projection; no slice selection was used. A symmetric 32 by 32 k-space matrix was covered corresponding to a 96 mm field of view and 3 mm in-plane resolution. The two $$\frac{\pi}{2}$$

RP pulses were identical, each with a ~5 ms duration. As discussed above, count rates were acquired with two different delays in order to construct the complex k-space data. 5 ms and (35+0.13) ms delays were used for measuring the real and imaginary spin moments, respectively. Imaging gradients were applied immediately after the first RF pulse and finished within the ~35 ms period, much less than the T$_2$ of approximately 200 ms. The total number of excitations needed for a complete image was 2048. Data were acquired using all three detectors. When the sample was not polarized, the 164 keV gamma count rate was ~13 kHz in each detector.

Prior to the acquisition of each point in k space, the sample was polarized for 90 seconds, and reached a polarization level of 65%. The count rate was next measured for 10 seconds providing data that were important for normalization during image reconstruction. The laser beam was then blocked, and the pulse sequence of FIG. 4 was applied, and data were acquired for 14 s. The laser was then unblocked, and the cycle was repeated. The acquisition of a complete image took ~66 hrs. For image a) shown in FIG. 12, the average of two complete images was used. Most of the time was just for polarizing $^{131m}$Xe and was not required by the imaging technique itself. The total data-taking time to acquire a single complete image was ~8 hrs for each detector, which may be considered long in comparison to the duration of a conventional MRI scan. In alternative embodiments, 100 mCi of $^{131m}$Xe may be used, and two longitudinal detectors may be used instead of one, such that the same statistics may have been acquired with 3.6 minutes of actual data acquisition.

Image Reconstruction

The data from each detector were analyzed independently. Three ADC channels recorded the output voltage of the gate/delay generator as a function of time for each of the three detectors. For each point in k space, and each detector, two 14 s data strings (corresponding to the real and imaginary spin moments) were used. Since the $^{131m}$Xe polarization, and thus the SNR, dropped during the 14 s of data taking time because of Ti relaxation, each count string was segmented into seven 2 s blocks and analyzed separately. The count rate in each 2 s time block was normalized with respect to the count rate of the preceding baseline measurement to account for the decay of $^{131m}$Xe during the long imaging procedure. For each time block, a 32 by 32 k space matrix was constructed, and the value of each k space point was determined by the normalized count rates measured with the two different delays according to Eq. 59 below.

$$A(\vec{k}) = a_2 \int \left( \rho(\vec{r}) e^{-2\pi i \frac{\vec{k} \cdot \vec{r}}{k}} d^3\vec{r} + (1+i)a_0 \int \rho(\vec{r}) d^3\vec{r} + A_0 \right) \quad (59)$$

The k-space offset $A_0$ should be constant in the ideal case. However, this offset changed slowly during the imaging procedure, perhaps due to some slow drift in the signal acquisition chain. To account for this drift, the offset was estimated separately for each column with the same $k_x$ by using the values at large $k_y$. ($k_x$ was the outer loop, and $k_y$ was the inner loop for traversing the k space). After subtracting the slowly varying offset, seven images were reconstructed for each detector by Fourier transform of these k space matrices. Each set of images were then combined into a single one with appropriate weighting factors to account for statistics. Finally, the three images from the longitudinal and the transverse detectors were combined with weighting factors determined by Eq. 60 and the corresponding count rate.

$$W_c'\left(\vec{k}, \vec{r}\right) = a_0 + \frac{1}{4}a_2[\cos(2\theta_d) - 1] + \frac{1}{4}a_2[3\cos(2\theta_d) + 1]\cos(2\pi\vec{k} \cdot \vec{r}) \quad (60)$$

Results

The non-imaging studies resulted in the observations illustrated in FIG. 13 and FIG. 14. Anisotropic emission of gamma rays was characterized using Eq. 1 above. The plot a) in FIG. 14 represents 164 keV gamma transition of $^{131m}$Xe for polarizations of 0%, 70% and 100% respectively. Before imaging, spectroscopic measurements in which gamma detection was used to directly observe polarized $^{131m}$Xe nuclear spin precession were performed. Initially, with unpolarized spins, the count rates were roughly equal in all detectors. The spins were polarized along the z axis using the technique of spin-exchange optical pumping, and the buildup of polarization was monitored by observing a decrease (increase) in the count rate of the longitudinal (transverse) detector (plot b) of FIG. 14). Once the polarization reached 60-70%, the spins were tipped into the transverse plane using a $$\frac{\pi}{2}$$

RF pulse. the spin orientation, and therefore the anisotropic emission distribution (w($\theta_1$), began to precess about the magnetic field, resulting in an oscillating count rate in the transverse detectors (plot c) of FIG. 14).

In graph a) of FIG. 13, a Free Induction Decay (FID) is shown in which the spins were first tipped by $$\frac{\pi}{2}$$

with respect to the magnetic holding field and then allowed to precess freely. Because of the anisotropy, as the spins rotated, the count rates in the detectors changed. The transverse relaxation time ($T_2$) was on the order of 200 ms. While $T_2$ was much shorter than expectations of tens of seconds based on estimates of magnetic-field inhomogeneities, it may have been limited by quadrupole interactions. In b), it is shown that precession under spin-locking conditions, during which the spins were locked to the (rotating) RF field. During spin locking, spin relaxation is governed by the longitudinal spin-relaxation time in the rotating frame ($T_{1\rho}$), which for us was on the order of ten seconds. In both graph a) and b) multiple averages were acquired to obtain good statistics. When polarized spins are subjected to a transverse resonant RF field $B_1$, they begin to precess about $B_1$ with a Larmor frequency determined by the RF strength. In pulsed NMR, the RF is only left on long enough for the spins to precess by a specific angle, such as a $$\frac{\pi}{2}$$

pulse that is used to tip the spins into the transverse plane. If the RF is left on, however, the spins continue to precess, and the polarization along the longitudinal axis oscillates. This phenomenon is known as Rabi oscillation ([7]). Normally these oscillations are not directly observed because the applied RF would overwhelm the detection electronics. When detecting gamma rays, however, it is irrelevant whether the RF is on or off, and the oscillations can be monitored directly.

In FIG. 13, b) shows the count rate in the longitudinal detector during Rabi oscillations after accumulating multiple averages. The signal has been mixed down to roughly 3 Hz, and low frequency components have been filtered out. One or more "beat" frequencies are clearly visible, and the Fourier transform of the (unmixed) signal, shown in c), shows at least two distinct frequency peaks. Since $^{131m}$Xe has a spin of 1

$$\frac{1}{2},$$

a natural explanation for the beat frequencies is that some type of interaction has shifted some of the magnetic sublevels, resulting in multiple, but closely spaced, NMR lines. This may also explain the short $T_2$ in graph a) of FIG. 13. The data in graph b) of FIG. 13 is reminiscent of those obtained by Wu et al. ([8]) who studied Rabi oscillations using optical techniques in a sample of (non-radioactive) $^{131}$Xe (which has a spin $$\frac{3}{2}.$$

Wu et al. ([8]) demonstrated that the multiple peaks were due to interactions between the Xe nuclear electric quadrupole moment and electric field gradients at the glass container walls. These data demonstrate the ability to resolve fine NMR spectral differences using gamma detection.

The methods described above generated image a) illustrated in FIG. 12. Data were acquired using the pulse sequence in FIG. 4 which had a magnetic-filed gradient described by Eq. 16 above. In principle, the resulting time-varying count rates in the transverse detectors can yield sufficient information for the later reconstruction of an image. Because of the short $T_2^*$, however, limited statistics were obtained before the spins lost their coherence. To overcome this limitation, a second $$\frac{\pi}{2}$$

pulse was applied after a time $t_{delay}$, which rotated the spins in the x-y plane into the y-z plane. As described in the sections above, the resulting constant count rate in the longitudinal detector, which was monitored for 15 seconds, provided the required imaging information. For each point in k space, this cycle was repeated twice using two values of $t_{delay}$ that differ from one another by $$\frac{1}{8}\tau_{Larmor}.$$

The resulting count rates are referred to herein as the real and imaginary spin moments, $S\Re(\vec{k})$ and $S_\Im(\vec{k})$ respectively, and define the function $$A(\vec{k}) = S\Re(\vec{k}) + iS_\Im(\vec{k}) + A_0 \quad (61)$$

where $A_0$ is a complex constant. It is always possible to choose $A_0$ such that $$A(\vec{k}) = C\int \rho(\vec{r})e^{i\vec{k}\cdot\vec{r}}d^3\vec{r} \quad (62)$$

where $\rho(\vec{r})$ is the density of polarized spins as a function of position $\vec{r}$ and C is a constant By taking the Fourier transform of Eq. 62, the density distribution $\rho(\vec{r})$ can be determined. This strategy allows one to construct an image, as shown in image a) of FIG. 12 using MR-based spatial encoding without directly observing spin precession in the transverse plane, which is a unique characteristic of PNI with gamma detection.

CONCLUSION

The specific configurations, choice of materials and the size and shape of various elements can be varied according to particular design specifications or constraints requiring a system or method constructed according to the principles of the present disclosure. Such changes are intended to be embraced within the scope of the present disclosure. The presently disclosed embodiments, therefore, are considered in all respects to be illustrative and not restrictive. The scope of the present disclosure is indicated by the appended claims, rather than the foregoing description, and all changes that come within the meaning and range of equivalents thereof are intended to be embraced therein.

REFERENCE LIST

[1] Thad G. Walker and William Happer, *Spin-exchange optical pumping of noble-gas nuclei, Reviews of Modern Physics* 69, 629 (1997).

[2] M. S. Albert, G. D. Cates, B. Driehuys, W. Happer, B. Saam, C. S. Springer Jr., and A. Wishnia, *Biological Magnetic Resonance Imaging Using Laser-Polarized $^{129}$Xe*, Nature 370, 199 (1994).

[3] F. P. Calaprice, W. Happer, D. F. Schreiber, M. M. Lowry, E. Miron and X. Zeng, *Nuclear Alignments and Magnetic Moments of 133Xe, 133mXe, 131mXe by Spin Exchange with Optically Pumped87Rb*, Phys. Rev. Lett. 54, 174 (1985).

[4] B. Driehuys, G. D. Cates, E. Miron, K. Sauer, D. K. Walter, and W. Happer, *High-Volume Production of Laser-Polarized $^{129}$Xe*, Appl. Phys. Lett. 69, 1668 (1996).

[5] T. Yamazaki, Nuclear Data Section A 3, 1 (1967).

[6] Yuan Zheng, Gordon D. Cates, William A. Tobias, John P. Mugler, III, G. Wilson Miller, *Very-Low-Field MRI of Laser Polarized Xenon-129*, Journal of Magnetic Resonance 249, 108 (2014).

[7] I. I. Rabi, Physical Review 51, 652 (1937).

[8] Z. Wu, W. Happer and J. Daniels, *Coherent Nucler-Spin Interactions of Adsorbed 131Xe gas with surfaces*, Physical Review Letters 59. 1480-1483 (1987).

What is claimed is:

1. A method for examining a subject, comprising:
polarizing nuclei of a radioactive substance such that the spins of the nuclei are oriented in a specific direction, to generate a polarized radioactive tracer with anisotropic gamma ray emission probability;
introducing the tracer into a subject;
applying at least one of radio frequency oscillating (RF) magnetic fields and spatially varying magnetic fields to the tracer in the subject that are configured to manipulate the orientation of the spins such as to manipulate the directional dependence of anisotropic gamma ray emission from the tracerin the subject;
detecting gamma rays from the gamma ray emission; and
obtaining, based on the detected gamma rays and properties associated with the gamma ray emission, at least one of imaging data and spectroscopic data associated with the tracer in the subject wherein the applying of at least one of radio frequency oscillating (RF) magnetic fields and spatially varying magnetic fields to the tracer in the subject includes applying the at least one of radio frequency oscillating (RF) magnetic fields and spatially varying magnetic fields to the tracer in the subject prior to the detecting of gamma rays from the gamma ray emission.

2. The method of claim 1, wherein obtaining at least one of imaging data and spectroscopic data associated with the tracer is performed such as to enable at least one of reconstructing an image corresponding to the spatial distribution of the tracer in the subject and measuring magnetic resonance properties of the tracer in the subject.

3. The method of claim 1, wherein obtaining at least one of imaging data and spectroscopic data associated with the tracer comprises determining count rates corresponding to the rate at which the gamma rays are detected.

4. The method of claim 3, wherein the determined count rates are associated with a time-independent probability of gamma emission along a particular direction.

5. The method of claim 3, wherein the determined count rates are associated with a time-dependent probability of gamma emission along a particular direction due to rotational motion of the nuclear spin orientation.

6. The method of claim 1, wherein the spatially varying magnetic fields correspond to pulses of magnetic field gradients.

7. The method of claim 6, wherein the pulses of magnetic field gradients correspond to pulses of static magnetic field gradients or pulses of RF magnetic field gradients.

8. The method of claim 7, wherein the pulses of static magnetic field gradients are applied to the tracer such that spatial information associated with distribution of the polarized radioactive tracer in the subject is encoded into the directional dependence of the gamma ray emission probability.

9. The method of claim 8, wherein:

the amplitude and direction of each static magnetic field gradient are characterized according to $$\vec{G} \equiv \frac{dB_z}{dx}\hat{x} + \frac{dB_z}{dy}\hat{y} + \frac{dB_z}{dz}\hat{z};$$

the time dependence of each applied gradient pulse is characterized by a function of time $\vec{G}(t)$;

the spatial information associated with the distribution of the tracer in the subject comprises spatial frequency components $\vec{k}$, each corresponding to an applied gradient pulse $\vec{G}(t)$ according to $$2\pi \vec{k} = 2\gamma \int \vec{G}(t) dt;$$

the spatial information further comprises complex-valued amplitudes $A(\vec{k})$ calculated based on count rates measured in at least one gamma detector in conjunction with the application of the corresponding gradient pulses; and a Fourier-transform relationship between the complex-valued amplitudes $A(\vec{k})$ and the spatial distribution $\rho(\vec{r})$ of the polarized tracer in the subject is characterized according to $$A(\vec{k}) \propto \int \rho(\vec{r}) e^{-i2\pi \vec{k}\cdot\vec{r}}$$

such as to allow the spatial distribution $\rho(\vec{r})$ to be reconstructed based on the measured gamma count rates.

10. The method of claim 1, wherein the obtaining of at least one of imaging data and spectroscopic data is performed while the RF magnetic fields are being applied.

11. The method of claim 10, wherein obtaining at least one of imaging data and spectroscopic data is performed during Rabi oscillations induced by the applied RF magnetic fields and wherein time-dependent count rates associated with Rabi oscillations are measured using at least one of longitudinally oriented and non-longitudinally oriented gamma detectors.

12. The method of claim 11, wherein the obtaining of spectroscopic data comprises measuring Rabi precession frequencies in the subject.

13. The method of claim 1, wherein the spectroscopic data is associated with nuclear magnetic resonance spectroscopy and comprises at least one of chemical-shift frequencies, spectral intensities, and spin-relaxation rates.

14. The method of claim 1, wherein the emitted gamma rays are detected using a single gamma detector oriented in a specific direction.

15. The method of claim 1, wherein the emitted gamma rays are detected using a plurality of gamma detectors oriented in a plurality of specific directions such as to detect a larger total fraction of the emitted gamma rays and measure directional differences in detected count rates associated with anisotropic gamma emission from the polarized radioactive tracer.

16. The method of claim 1, wherein the emitted gamma rays are detected using at least one gamma detector without a collimator.

17. The method of claim 1, wherein polarizing the nuclei of the radioactive substance comprises performing spin-exchange optical pumping or dynamic nuclear polarization.

18. The method of claim 1, wherein polarizing the nuclei of the radioactive substance comprises polarizing the nuclei such that the nuclei are hyperpolarized.

19. The method of claim 1, wherein the tracer has a nuclear spin greater than 1/2.

20. The method of claim 1, wherein the radioactive substance is an isotope of a noble gas.

21. The method of claim 1, further comprising, based on the obtained at least one of the imaging data and spectroscopic data, determining one or more characteristics of a physiological function or anatomical structure in an area of interest of the subject.

22. The method of claim 21, wherein determining the one or more characteristics of the physiological function or anatomical structure in the area of interest comprises identifying a predetermined signature associated with a biological compartment or chemical environment in the area of interest.

23. The method of claim 1, wherein the subject is a non-living object and the method further comprises determining, based on the obtained at least one of the imaging data and spectroscopic data, one or more characteristics of the non-living object.

24. The method of claim 1, wherein applying at least one of RF magnetic fields and spatially varying magnetic fields to the tracer to manipulate the orientation of the spins comprises applying a pulse sequence configured such as to allow acquisition of imaging information by measurement of gamma count rates associated with time-independent probabilities of gamma emission along particular directions.

25. The method of claim 24, wherein applying the pulse sequence comprises:
(a) applying a first RF pulse to tip spins of the tracer from a longitudinal direction into a transverse direction;
(b) applying a magnetic field gradient pulse of predetermined size such as to encode spatial imaging information associated with the tracer;
(c) applying a second RF pulse at a predetermined time such as to rotate a particular transverse spin component into the longitudinal direction; and
(d) measuring count rates using at least one gamma detector.

26. The method of claim 25, further comprising performing (a)-(d) a predetermined number of times, with varying size of the applied magnetic field gradient pulse.

27. The method of claim 25, wherein each of the first RF pulse and second RF pulse is a $\pi/2$ pulse.

28. The method of claim 1, wherein applying at least one of RF magnetic fields and spatially varying magnetic fields to the tracer to manipulate the orientation of the spins comprises applying a pulse sequence configured such as to allow acquisition of spectroscopic information by measurement of gamma count rates associated with time-independent probabilities of gamma emission along particular directions.

29. The method of claim 28, wherein applying the pulse sequence comprises:
(a) applying a first RF pulse to tip spins of the tracer from a longitudinal direction into a transverse direction;
(b) waiting a predetermined time such as to encode spectroscopic information associated with the tracer;
(c) applying a second RF pulse at a predetermined time such as to rotate a particular transverse spin component into the longitudinal direction; and (d) measuring count rates using at least one gamma detector.

30. The method of claim 29, further comprising performing (a)-(d) a predetermined number of times, with varying wait time between respective first and second RF pulses.

31. The method of claim 29, wherein each of the first RF pulse and second RF pulse is a $\pi/2$ pulse.

32. The method of claim 1, wherein applying at least one of RF magnetic fields and spatially varying magnetic fields to the tracer to manipulate the orientation of the spins comprises applying a pulse sequence configured such as to allow acquisition of both spectroscopic and imaging information by measurement of gamma count rates associated with time-independent probabilities of gamma emission along particular directions.

33. The method of claim 32, wherein applying the pulse sequence comprises:
   (a) applying a first RF pulse to tip spins of the tracer from a longitudinal direction into a transverse direction;
   (b) applying a magnetic field gradient pulse of predetermined size such as to encode spatial imaging information associated with the tracer;
   (c) waiting a predetermined time duration such as to encode spectroscopic information associated with the tracer;
   (d) applying a second RF pulse at a predetermined time such as to rotate a particular transverse spin component into the longitudinal direction; and
   (e) measuring count rates using at least one gamma detector.

34. The method of claim 33, further comprising performing (a)-(e) a predetermined number of times, with varying sizes of the applied gradient pulse and time duration between respective first and second RF pulses.

35. The method of claim 33, wherein each of the first RF pulse and second RF pulse is a $\pi/2$ pulse.

36. The method of claim 1, wherein applying at least one of RF magnetic fields and spatially varying magnetic fields to the tracer to manipulate the orientation of the spins comprises applying a pulse sequence configured such as to allow acquisition of at least one of imaging information and spectroscopic information by measurement of gamma count rates associated with the time-varying probabilities of gamma emission along particular directions.

37. The method of claim 36, wherein applying the pulse sequence comprises:
   applying at least one RF pulse to tip spins of the tracer from a longitudinal direction into a transverse direction; and
   measuring count rates using at least one gamma detector while spins of the tracer are precessing in the transverse plane.

38. The method of claim 36, wherein applying the pulse sequence comprises:
   (a) applying at least one RF pulse to tip spins of the tracer from a longitudinal direction into a transverse direction;
   (b) applying at least one magnetic field gradient pulse of predetermined size such as to encode spatial imaging information associated with the tracer; and
   (c) measuring count rates using at least one gamma detector while spins of the tracer are precessing in the transverse plane.

39. The method of claim 38, further comprising performing (a)-(c) a predetermined number of times, with varying sizes of the applied gradient pulse.

* * * * *

UNITED STATES PATENT AND TRADEMARK OFFICE
CERTIFICATE OF CORRECTION

PATENT NO.        : 10,126,438 B2
APPLICATION NO.   : 14/859271
DATED             : November 13, 2018
INVENTOR(S)       : Gordon D. Cates, Jr. et al.

Page 1 of 1

It is certified that error appears in the above-identified patent and that said Letters Patent is hereby corrected as shown below:

In the Claims

In Claim 1 at Column 38, Line 29, the term "tracerin" should read --tracer in--.

Signed and Sealed this
Twenty-ninth Day of January, 2019

Andrei Iancu
*Director of the United States Patent and Trademark Office*